United States Patent [19]

Anderson et al.

[11] Patent Number: 5,279,294

[45] Date of Patent: * Jan. 18, 1994

[54] MEDICAL DIAGNOSTIC SYSTEM

[75] Inventors: Paul J. Anderson, Bloomington; Ross A. Jessen, Chaska; David R. Linde, Maple Grove; Richard E. Jones, Bloomington; Bert Walter, Mendota Heights; Paul E. Christenson, Apple Valley, all of Minn.

[73] Assignee: Cascade Medical, Inc., Eden Prairie, Minn.

[*] Notice: The portion of the term of this patent subsequent to Jan. 20, 2004 has been disclaimed.

[21] Appl. No.: 499,085

[22] Filed: Mar. 26, 1990

Related U.S. Application Data

[60] Continuation-in-part of Ser. No. 272,011, Nov. 16, 1988, abandoned, which is a division of Ser. No. 889,185, Jul. 25, 1986, Pat. No. 4,787,398, which is a continuation-in-part of Ser. No. 744,539, Aug. 13, 1991, Pat. No. 4,637,403, which is a continuation-in-part of Ser. No. 720,595, Jun. 25, 1991, Pat. No. 4,627,445.

[51] Int. Cl.$^5$ .................................................. A61B 5/14
[52] U.S. Cl. ...................................... 128/633; 128/770; 128/632
[58] Field of Search ............... 128/770, 771, 763, 636, 128/637, 633, 634, 632; 356/39–42; 606/181, 182

[56] References Cited

U.S. PATENT DOCUMENTS 4,637,403 1/1987 Garcia et al. .................. 128/770
4,787,398 11/1988 Garcia et al. .................. 128/770

Primary Examiner—David M. Shay
Attorney, Agent, or Firm—Hugh D. Jaeger

[57] ABSTRACT

Hand-held shirt-pocket portable instrument for quantitative measurement of glucose or analysis in biological fluids. The system accepts a disposable diagnostic reagent test device which has a reagent carrier and mode of identifying to the instrument the reagent lot characteristics. The instrument includes a housing structure having a visual LCD readout, a microprocessor, and photosensing circuitry which measures the change of color of the reagent carrier upon reaction in the reacting chemistry of the disposable test device. The housing also includes a spring arrangement for actuating a disposable lancet into the skin for generating blood. The disposable diagnostic reagent unit includes a configuration for transporting of the blood in the regent unit. The system includes verification and calibration sequences for the electronics, the chemistry of an unused disposable unit, the presence of a blood sample, and the ambient temperature. The system also provides for storing a plurality of analysis readings.

25 Claims, 31 Drawing Sheets

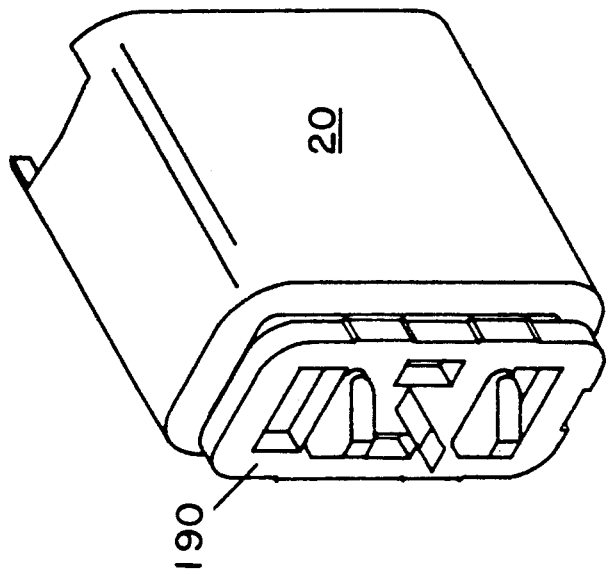
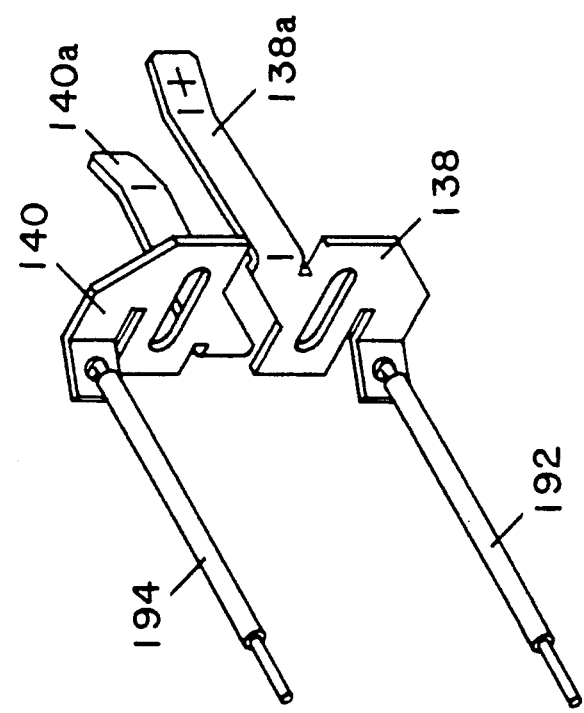
FIG.9

CLEARING DISPLAY MESSAGES

1. Remove ANSWER strip.
2. Close Optic Cover.
3. Pull back Sliding Button.
4. Press Release Button.

FIG.15

- HOt — Temperature too high. Begin again at 63°–95°F.
- CLd — Temperature too low. Begin again at 63°–95°F.
- LLL — Result lower than 40 mg/dL. See Instruction Manual.
- HHH — Result higher than 400 mg/dL. See Instruction Manual.
- (blank) — Batteries dead or ANSWER meter malfunctioning. See Instruction Manual.
- - - — Batteries are low, meter will function properly. Replace Batteries soon.
- EEE — Batteries too low. Replace Immediately.
- E-0 — Electronics error. See Instruction Manual.
- E-1 — Optic Cover not closed. Close Cover, begin again.
- E-1 (Continued) — Dirt on Optic Window or Calibration Pad. Clean, begin again. Electronic malfunction. See Instruction Manual.
- E-2 — ANSWER strip dislodged or removed after firing Lancet. Begin again with same ANSWER strip.
- E-3 — ANSWER strip dis-colored or used. Begin again with new ANSWER strip.
- E-3 (Continued) — ANSWER strip inserted upside down. Begin again with same ANSWER strip.
- E-4 — Too little blood applied within the time allotted to initiate countdown. Begin again with new ANSWER strip. No blood applied. Begin again with same ANSWER strip.
- E-5 — ANSWER strip dislodged or removed before firing LANCET. Reinsert immediately.
- E-6 — Too little blood applied to complete countdown. Repeat test with new ANSWER strip.
- E-7 — ANSWER strip not inserted within 3 minutes after Sliding Button was pulled back. Begin again with same ANSWER strip.
- E-8 — Release Button not pressed within 3 minutes after insertion of ANSWER strip. Begin again with same ANSWER strip.

MEDICAL DIAGNOSTIC SYSTEM

This application is a continuation-in-part of Ser. No. 07/272,011, filed Nov. 16, 1988, now abandoned, which is a divisional of Ser. No. 06/889,185, filed Jul. 25, 1986, now U.S. Pat. No. 4,787,398, which is a continuation-in-part of Ser. No. 06/744,539, filed Aug. 18, 1991 now U.S. Pat. No. 4,637,403, which is a continuation-in-part of Ser. No. 06/720,595, filed Jun. 25, 1991, now U.S. Pat. No. 4,627,445.

CROSS REFERENCES TO CO-PENDING APPLICATIONS

This relates to a patent application entitled "Regent Unit" by Anderson et al. U.S. Ser. No. 07/499,187, filed Mar. 26, 1990 for use with the Medical Diagnostic System of this patent application.

BACKGROUND OF THE INVENTION

1. Field of the Invention

The present invention pertains to a medical system, and more particularly, pertains to glucose medical monitoring diagnostic system for sampling and analyzing blood or any components of the blood for specific readings as to qualities of the blood. One specific use of the present invention is for sensing the accumulating of blood glucose for diabetics. The diagnostic system is a portable, pocket-size, battery operated, diagnostic system including a disposable diagnostic reagent unit and a disposable lancet.

2. Description of the Prior Art

Prior art blood glucose devices have operated on the principle of taking blood from an individual by a variety of methods, such as by a separate needle or lancing device. An individual then had to coat a separate unit carrying chemistry with the blood, time the chemical reaction for about 60 seconds, wipe or remove the blood sample from the unit, and insert the blood-coated unit into a blood glucose meter or make a visual personal comparison against a color standard.

There are numerous blood glucose meters in the marketplace, and most of the instruments consume physical space and are not easily pocketable. The instruments usually have to be carried in a large handbag, or a individual's briefcase, or left at home such as in the bathroom or the bedroom, or on a counter or a table.

The prior art medical apparatuses for sensing blood glucose required that an individual have separately available a needle or lance for extracting blood from the individual, units carrying blood chemistry for creating a chemical reaction with respect to the blood glucose and changing color, and a blood glucose meter for reading the change in color indicating the blood glucose level. The level of blood glucose, when measured by a glucometer, is read from a unit carrying the blood chemistry through the well known process of reflectometers based on the principle of glucose oxidation.

Some of the monitor/reagent unit systems that are now available on the market have multiple sequential steps that the patient must follow at exact time intervals. Each step is subject to error by the patient. As in most monitors, it is the patient's responsibility to periodically calibrate the monitor against known color standards; validate the efficacy of the reagent units and technique by immersing the units in a control solution of known glucose content; and, then comparing the color change visually against the color standard or by using a calibrated monitor. These types of prior art systems are subject of course to human error.

The procedure for obtaining accurate results from the time a drop of blood is placed on a reagent unit pad to the time the pad color change may be read in the glucose monitor is as now described. The patient must stick himself/herself with a lancet. A drop of blood must be squeezed to the surface of the skin. The blood must then be carefully placed on the reagent pad, making sure to cover the pad completely and that the pad is never touched by the finger of the patient to prevent contamination. Once the sample has been applied to the surface of the reagent pad, the patient must press a timer on the monitor. At the end of the timing, the patient must wipe, blot or wash the unit off, using a careful technique. And for most units, the patient must place the reacted reagent unit into the monitor, and press a test button or close a hatch to obtain results. Prior art commercially available comparable reagent units or monitors require operator intervention in a prescribed sequence at exact time intervals. The prior art monitors are subject to operator error, sequence errors, timing errors, and technique errors.

The prior art reagent units are also subject to contamination which may affect accuracy of measurement.

A representative patent is U.S. Pat. No. 4,787,398, same assignee on this patent entitled "Glucose Medical Monitoring System", issued on Nov. 29, 1988.

The present invention overcomes the disadvantages of the prior art by providing an integrated hand-held pocketable blood glucose monitoring meter which includes an attachable disposable lancet, reagent test device for blood glucose. unit carrying a chemical reagent chemistry, and a wick for, transporting the blood to the blood sensing reagent, resulting in a readout of a level of the blood glucose.

SUMMARY OF THE INVENTION

One general purpose of the present invention is a portable, shirt-pocket-size, battery-operated diagnostic system for use by health professionals and/or lay patients for the detection and measurement of certain selected chemical agents or substances for the purpose of diagnosis and/or treatment of disease. The system application is not restricted to use with human beings as to the sampling of blood glucose. The system may also be extended to veterinary medicine animals, and can also have uses in the agricultural field, such as measurement of glucose in grapes in the wine industry by way of example. One such medical application is for insulin dependent and non-insulin dependent diabetics for the measurement of glucose in serum, plasma, and/or whole blood. the particular quantity to be measured is glucose through the principles of either reflectance, absorption or potentiometric measurement by electronic circuitry although other quantities can be measured.

Another purpose of the present invention is to provide a hand-held pocketable medical measurement system including the engaging of a disposable lancet and a disposable diagnostic reagent unit carrying the blood sensing reagent for sensing readings of the blood, such as blood glucose level. The medical system is cost effective and simple to operate by an individual. The reading, such as an individual's glucose level, is displayed on an LCD display on the side of a housing of the medical system which approximates the size of an ordinary page highlighter which can be carried in an individual's shirt pocket. The disposable diagnostic reagent units in sterile packages and disposable lancets can be carried in a corresponding packets. The housing structure resembling a page highlighter contains the hand-held pocketable medical system. A like housing structure resembling a highlighter carriers the extra supply of disposable units. The design of the present invention provides for the utmost peace of mind for the individual.

According to one embodiment of the present invention, there is provided a hand-held pocketable medical system including an electromechanical structure for actuating a disposable lancet about a disposable diagnostic reagent unit which engages onto the system. The disposable diagnostic reagent unit enables a blood sample inside a finger or on the finger surface to be transferred to the blood reagent chemistry. The electromechanical structure includes a spring actuated configuration for movement of a hammer mechanism. The disposable lancet unit and diagnostic reagent unit engage and slide into the end of the hand-held pocketable medical system, and are easily releasable and disposable after a single use. The disposable lancet can be reused as may be required.

The hand-held medical system includes a light tight compartment with photosensing electronics connected to a microprocessor for analyzing the properties of the blood sensing chemistry in the disposable diagnostic reagent unit, and for displaying a readout and storing previous readouts. The electronics includes verification sequences for verifying operability of the electronics including annunciating of a low battery condition, for verifying the condition of a unused disposable unit, for verifying the presence of a blood sample and for subsequently providing multiple readings to provide for an averaging of results. The microprocessor can be programmed to measure other quantities.

According to other embodiments of the present invention, there is provided a disposable diagnostic reagent unit with a transporting action where a wick serves as the transport structure for the blood. There is also provided a disposable lancet unit in the hand held medical device for the piercing of an individuals skin.

One significant aspect and feature of the present invention is a hand-held pocketable diagnostic medical monitoring system which is utilized for extracting a blood sample from the body, subjecting the sample to chemical analysis, and visually displaying the numerical results to the individual. A disposable diagnostic reagent unit carries the blood sensing chemistry consisting of a reagent unit for either delivering blood to the reagent or for causing the reagent to be delivered to the blood. Additional disposable units can be carried in a corresponding structure similar to that of the medical system.

Another significant aspect and feature of the present invention is a housing like structure which is electromechanical, and where a button is pushed for actuating a firing mechanism in the housing structure against the disposable lancet contained therein through the spring driven structure. A hammer return spring returns the firing mechanism back to an original rest position and at about the same time, a return spring removes the sharp point of the lancet from the finger.

A further significant aspect and feature of the present invention is a hand-held pocketable diagnostic medical monitoring system which provides blood glucose readings where the disposable diagnostic reagent unit carries glucose-oxidase or like chemical reagent. Once the reagent material undergoes a colorimetric, potentiometric, or absorption action proportional to the blood glucose concentration, the microprocessor circuitry through the reflectance colorimeter provides for subsequent processing of the photosensing of the blood chemistry for displaying of the results on an LCD display.

Another significant aspect and feature of the present invention is a system which utilizes a slidable disposable diagnostic reagent unit. The reagent unit is a transport mechanism for transporting a fluid or liquid to the reagent unit.

Still another significant aspect and feature of the present invention is a system which inherently through mechanical operation pushes the disposal lance out of the housing to drop into a basket for disposal.

Having thus described embodiments of the present invention, it is principal objects hereof to provide a pocketable diagnostic medical monitoring system, including a disposable lancet and a disposable diagnostic reagent unit which carries blood sensing reagent material and which engages onto the system for providing a subsequent readout on a visual display of the system of a quality of the blood by the system. The system can be broadly extended to a system for measurement of a quantity of a substance in a particular fluid or material, and is not to be construed as strictly limited to medical applications, as the system can be used in industry, commercial, agricultural, consumer or even veterinary environments as examples.

One object of the present invention is to provide a hand-held pocketable diagnostic medical monitoring system with a disposable lancet and a disposable diagnostic reagent unit which engages onto the electromechanical assembly of the medical system. The disposable diagnostic reagent unit carries blood sensing reagent material for sensing components of the blood for qualities such as glucose level. Other qualities of fluid which can be measured are cholesterol, urea, nitrogen, hemoglobin, alcohol, protein or other qualities of the blood with appropriate reagent material.

Another object of the present invention is an electromechanical assembly which contains the microprocessor including the software, mechanical and electromechanical apparatus, batteries, and related circuitry that causes the electrical and electromechanical functional operation. The diagnostic is a disposable reagent unit containing the lancet for obtaining a blood sample, typically from a person's finger or toe, and a chemical impregnated reagent material that reacts with the presence of blood. The chemical reagent is sealed inside the reagent unit housing minimizing the effects of contamination from fingers, moisture, and light, thus improving accuracy and precision of measurement by stabilizing the oxidation reduction or chemical reaction of the reagent prior to use. The sensor in the assembly detects and measures via absorption, potentiometric, or reflectance analysis the amount of glucose or other blood quantity present. This analog data is provided and converted to a digital readout display quantifying glucose in milligrams per deciliter (mg/dl) or MMOL/L.

An additional object of the present invention is a self-contained automatic medical monitoring system. All operations and performance of the system are performed automatically, mechanically and electronically in proper sequences. Accuracy and precision of the measurement is enhanced because errors due to operator interpretation, operator technique, and timing of events, are removed from operator control because of microprocessor based system operation and a lot to lot as well as a test strip calibration.

Still another object of the present invention is a medical diagnostic system which is software controlled and software intelligent. The system is selfcalibrating through control commands by the software, and also based on a lot to lot material in the reagent unit and a calibration square on the inside of the dust cover.

DESCRIPTION OF THE PREFERRED EMBODIMENTS

Other objects and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 9 illustrates a perspective view of the battery case;

Figure 13:
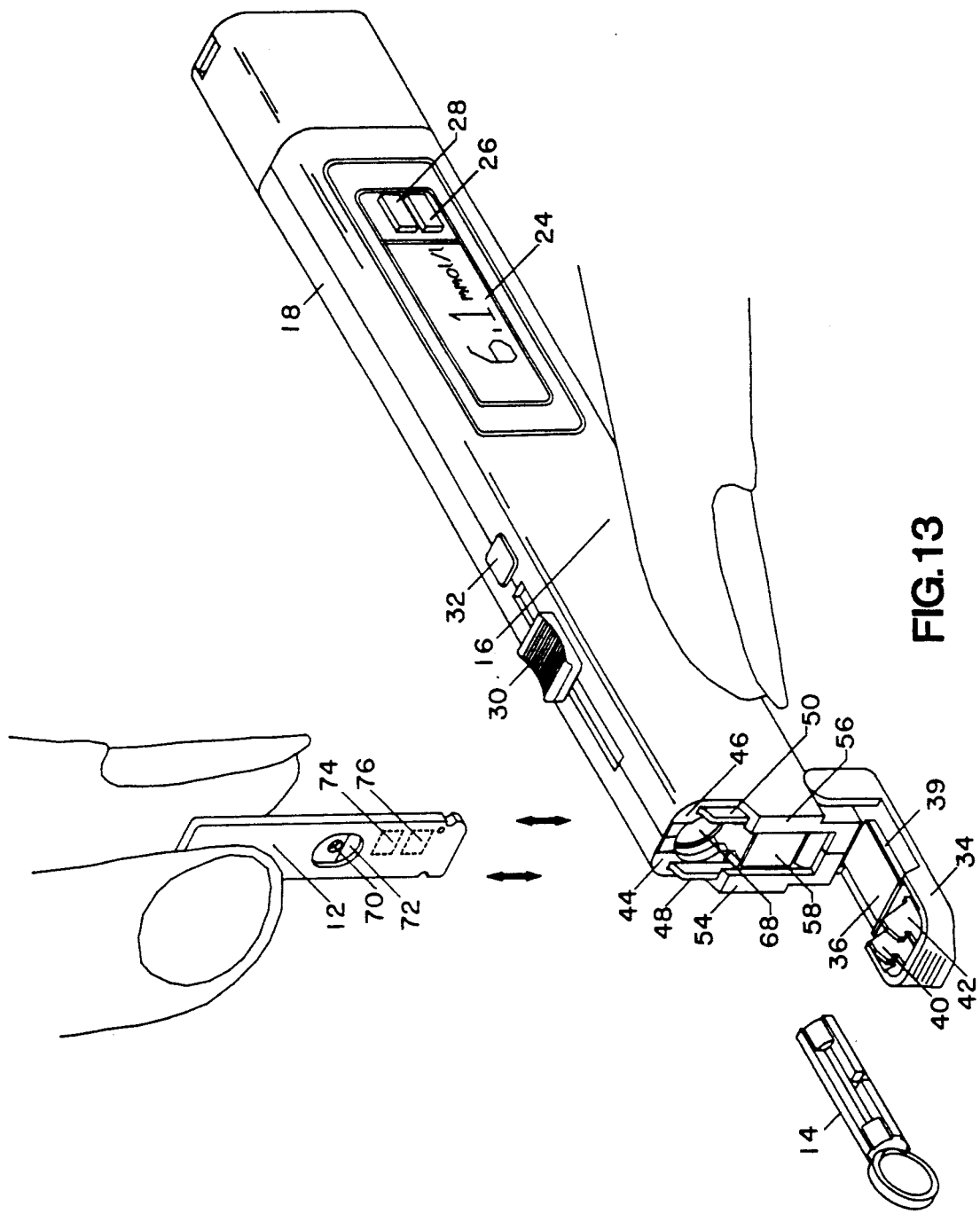

FIGS. 12A1-12A2, 12B1-12B2 and 12C illustrate an electrical circuit schematic diagram of the medical diagnostic system;

FIG. 13 illustrates loading of the medical diagnostic system;

FIG. 14A-14I illustrate component positioning during operation of the medical diagnostic system;

FIG. 15 illustrates display messages.

DESCRIPTION OF THE PREFERRED EMBODIMENTS

Figure 1:
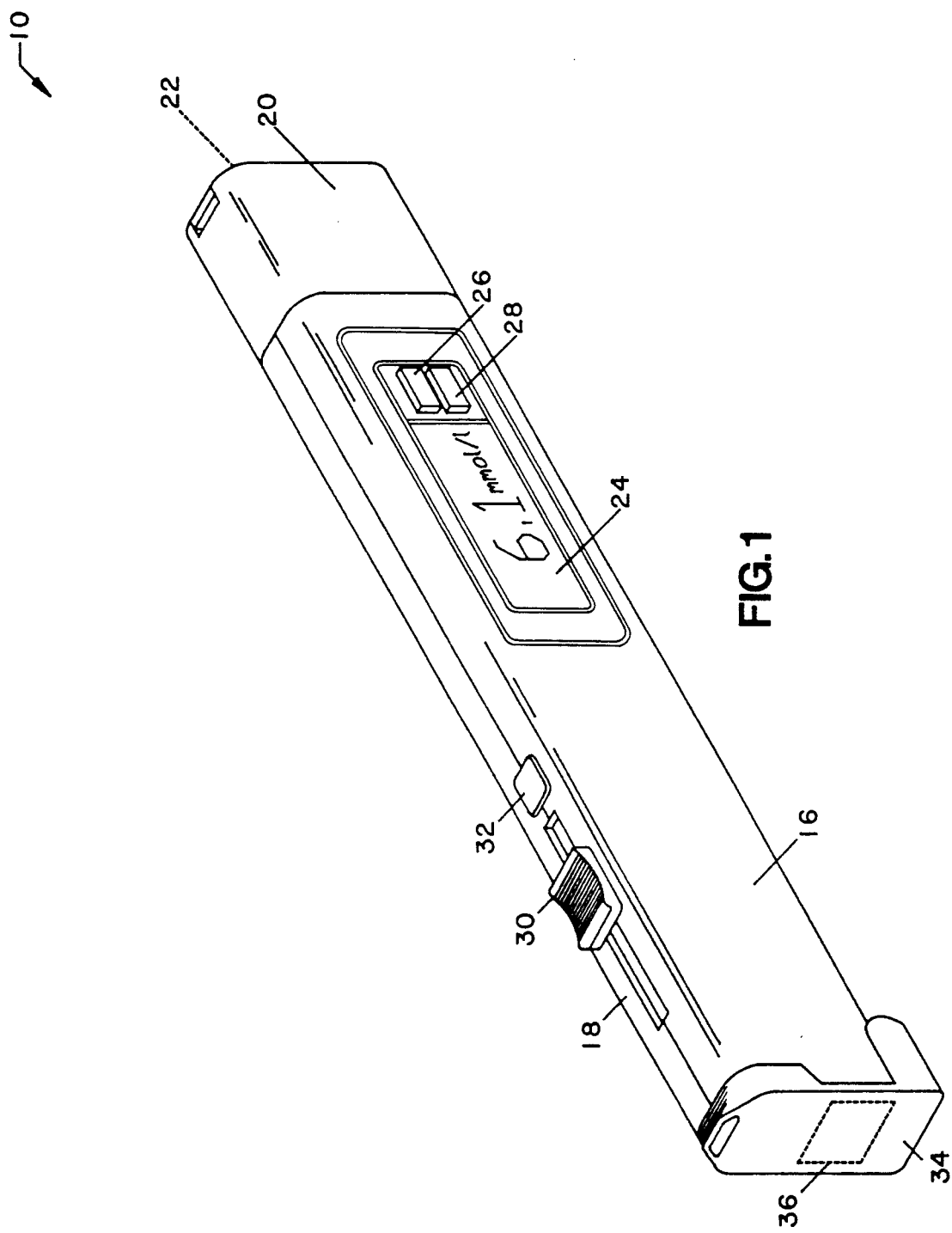
FIG. 1 illustrates a perspective view of an embodiment of a glucose medical monitoring system.

FIG. 1 illustrates a perspective view of a portable pocketable glucose medical diagnostic system 10 including a disposable diagnostic reagent unit 12 as illustrated and later described in particular detail in FIG. 4. Externally visible components of the system 10 include front and back housing halves 16 and 18 respectively which enclose the electromechanical structure as later described in detail and, a battery case 20 and battery cover 22. An LCD or like visual readout 24 displays the glucose levels, time, battery condition, stored values in memory, and other mode operational displays as later described in detail. Conductive rubber keypad buttons 26 and 28 position adjacent to the LCD readout 24. A actuator button 30 and a release button 32 locate on the top side of the glucose medical monitoring system 10 for subsequent cocking and releasing of a firing mechanism as later described in detail in the figures.

Figure 2:
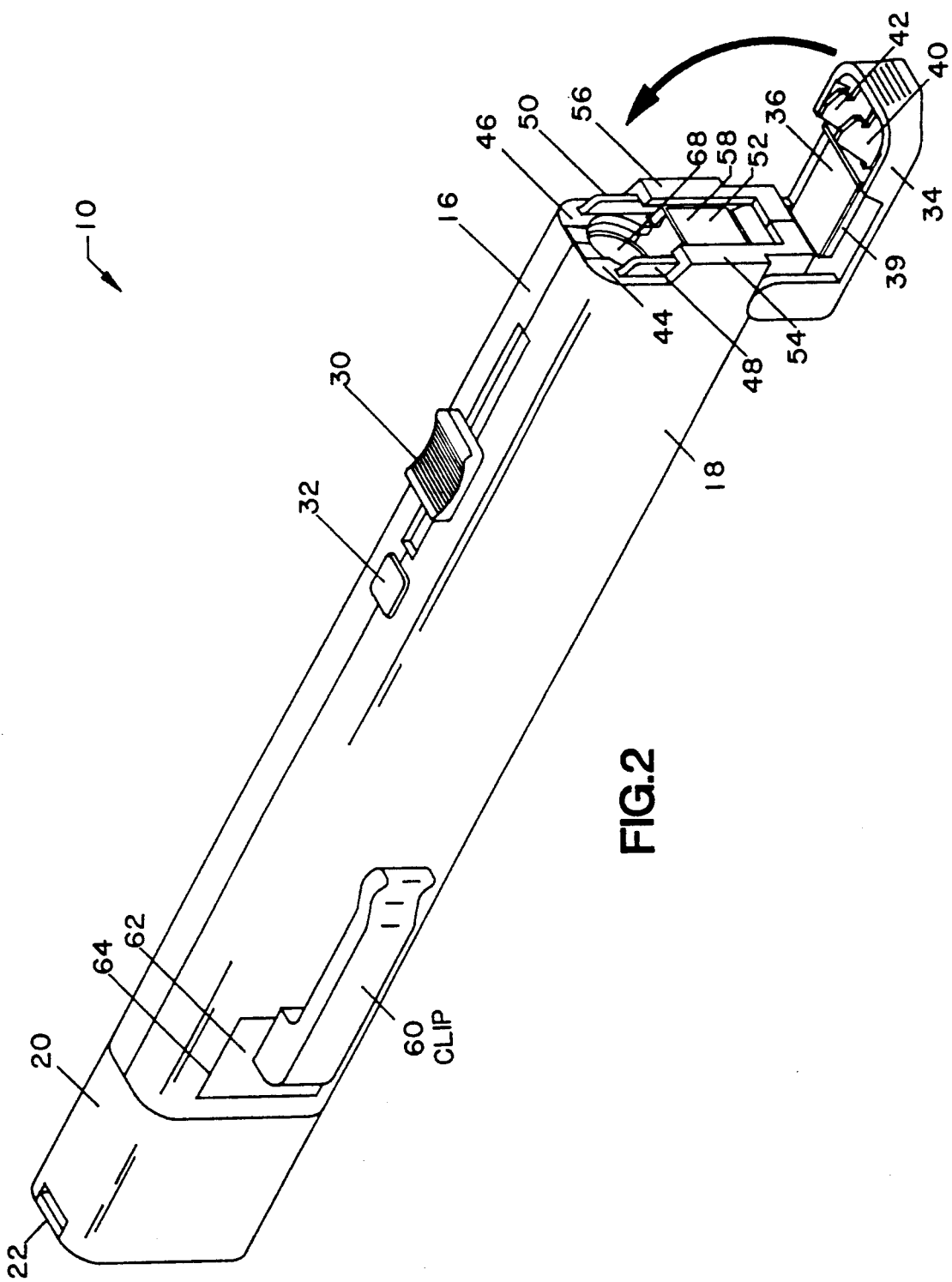
FIG. 2 illustrates a perspective view of the backside of the medical diagnostic system.
Figure 8:
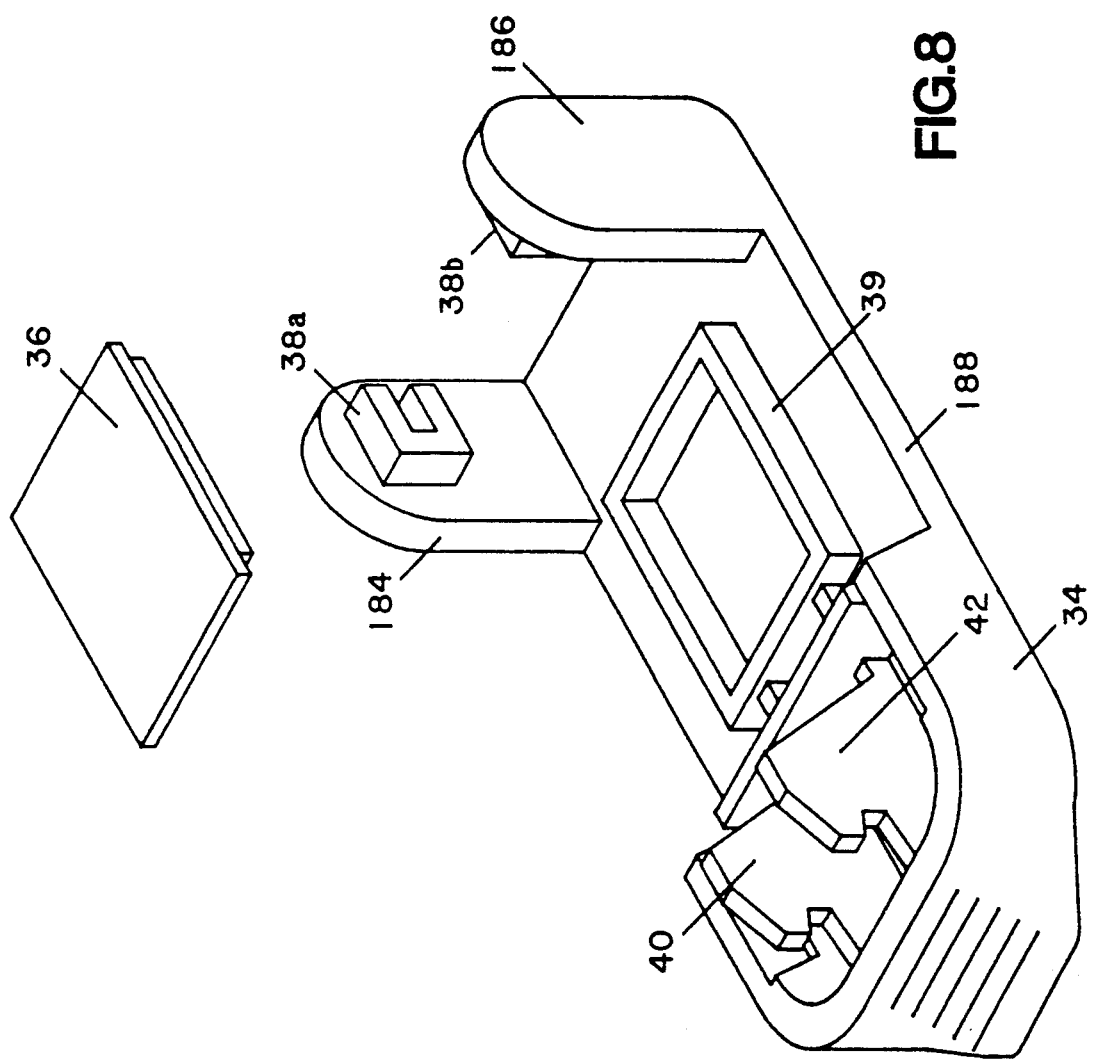
FIG. 8 illustrates a perspective view of the dust cover.

FIG. 2 illustrates a perspective in view of the portable pocketable glucose medical diagnostic system 10, where all numerals correspond to those elements previously described. The flush rotatable protective dust cover 34 includes an interior mounted color reference calibration unit 36 and rotates on pivot blocks 38a-38b of FIG. 8, and conforms to the front housing 16 and the back housing 18 halves. The dust cover 34 includes a rectangular frame 39 for the accommodation of the interior mounted color reference color calibration unit 36 as also illustrated in FIG. 8. Later members 40 and 42 extend vertically from the interior side of the dust cover 34 and latch with the catches 44 and 46 at the upper edges of the rear and front housing halves 18 and 16 respectively. Vertical guide bars 48 and 50 at the ends of the rear and front housing halves 18 and 16 align along the outer surfaces of the latches 40 and 42 to align the dust cover 34 with the ends of the combined case halves 18 and 16. The rectangular frame 39 containing the color reference calibration unit 36 aligns in a rectangular hole 52 between vertical end bars 54 and 56 at the ends of the rear and front housing halves 18 and 16 respectively. An optics window 58 aligns with the rectangular hole 52 and also with the color reference calibration unit 36 when the dust cover 34 is rotated and latched in the closed position.

A clip 60 with a square mounting pad 62 frictionally engages a corresponding size hole 64 in the rear housing half 18.

Figure 3:
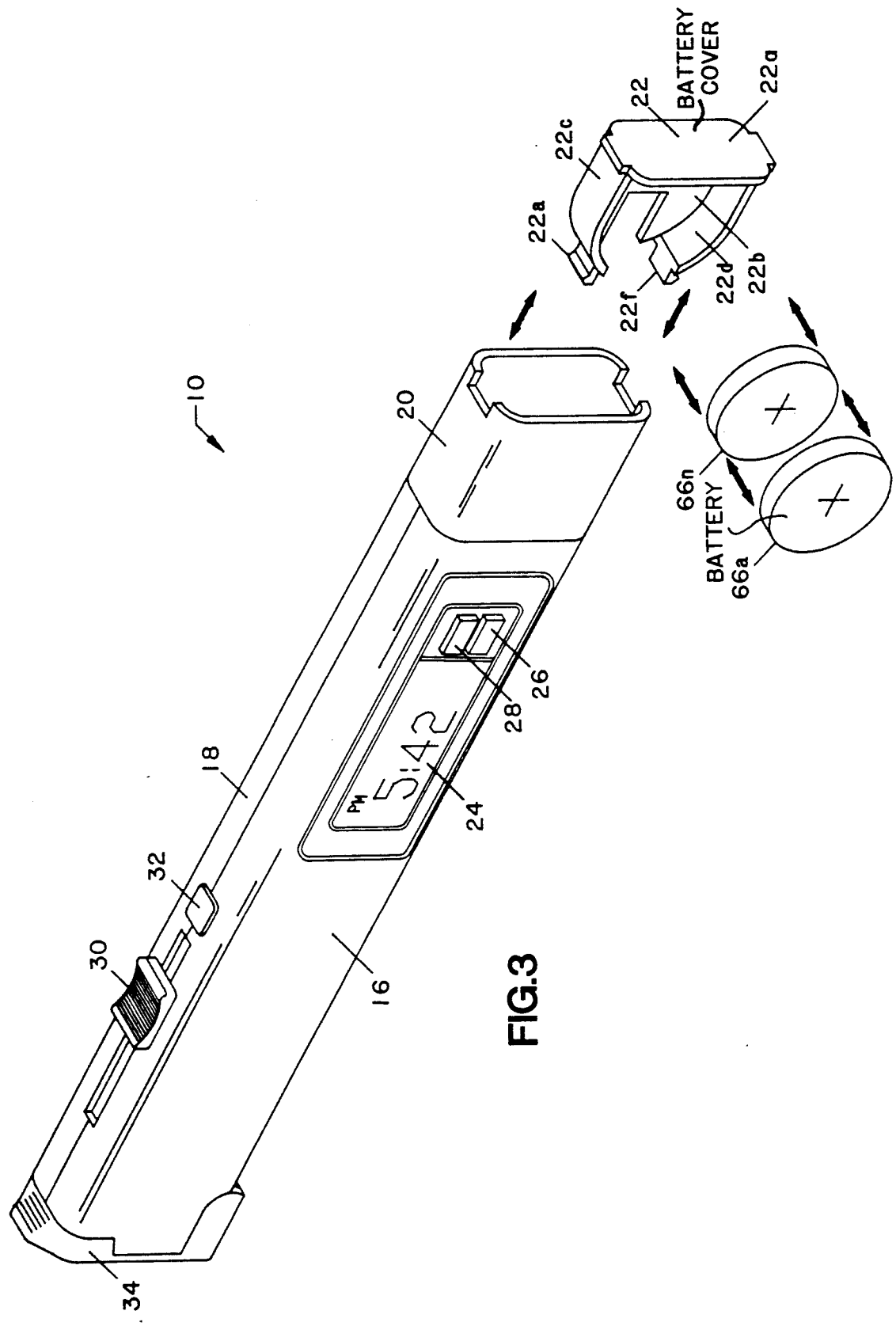
FIG. 3 illustrates a perspective view of the medical diagnostic system showing the battery case.

FIG. 3 illustrates a perspective view of the portable pocketable glucose medical diagnostic system 10, where all numerals correspond to those elements previously described illustrated in particular is the battery cover 22. The cover includes a back surface 22a and a side surface 22b between upper and lower curved surfaces 22c and 22d. Upper and lower curved surfaces 22c and 22d include end latch members 22e and 22f for snap engagement of the battery cover 22 within the battery case 20. The battery cover 22 members 22a, 22b, 22c and 22d form a carriage member into which a plurality of batteries 66a-66n are contained. The battery cover 22 and batteries 66a-66n engage within the battery case 20. The batteries 66a-66n are connected as later described in detail in FIG. 5.

Figure 4:
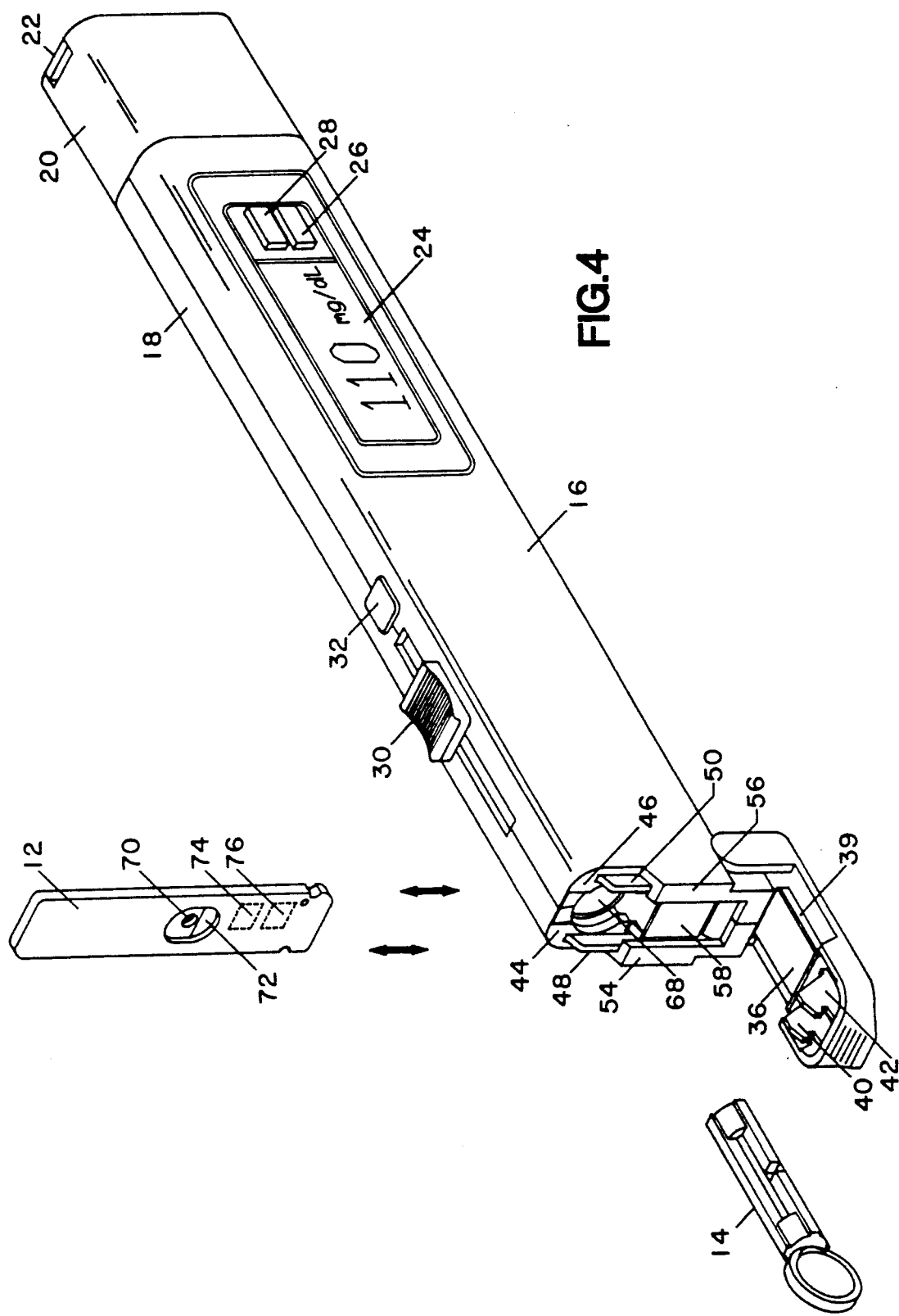
FIG. 4 illustrates a perspective view of the medical diagnostic system ready to receive a disposable lancet and a disposable diagnostic reagent strip.

FIG. 4 illustrates a perspective view of the portable pocketable glucose medical diagnostic system 10 with a disposable diagnostic reagent unit 12 and a disposable lancet 14, where all numerals correspond to those elements previously described. The disposable lancet 14 is inserted into the firing mechanism assembly 68 of FIG. 5 through an orifice 68. Orifice 68 aligns beneath the catches 44 and 46 and between the guide 4 bars 48 and 50 and in the end of the front and rear housings 16 and 18. After the disposable lancet 14 is inserted through the orifice 68, the disposable diagnostic reagent unit 12 is inserted between guide bars 48 and 50, in front of the orifice 68 and catches 44 and 46 and behind the vertical end bars 54 and 56. The disposable reagent pad 12 includes a hole 70 and reagent pad 72 and windows 74 and 76 for viewing of the blood soaked reagent pad 72 by internal electronic viewing as later described in detail. The hole 70 in the disposable diagnostic reagent unit aligns with the lancet needle and the windows 74 and 76 align with the optics window 58 for electronic viewing.

Figure 5:
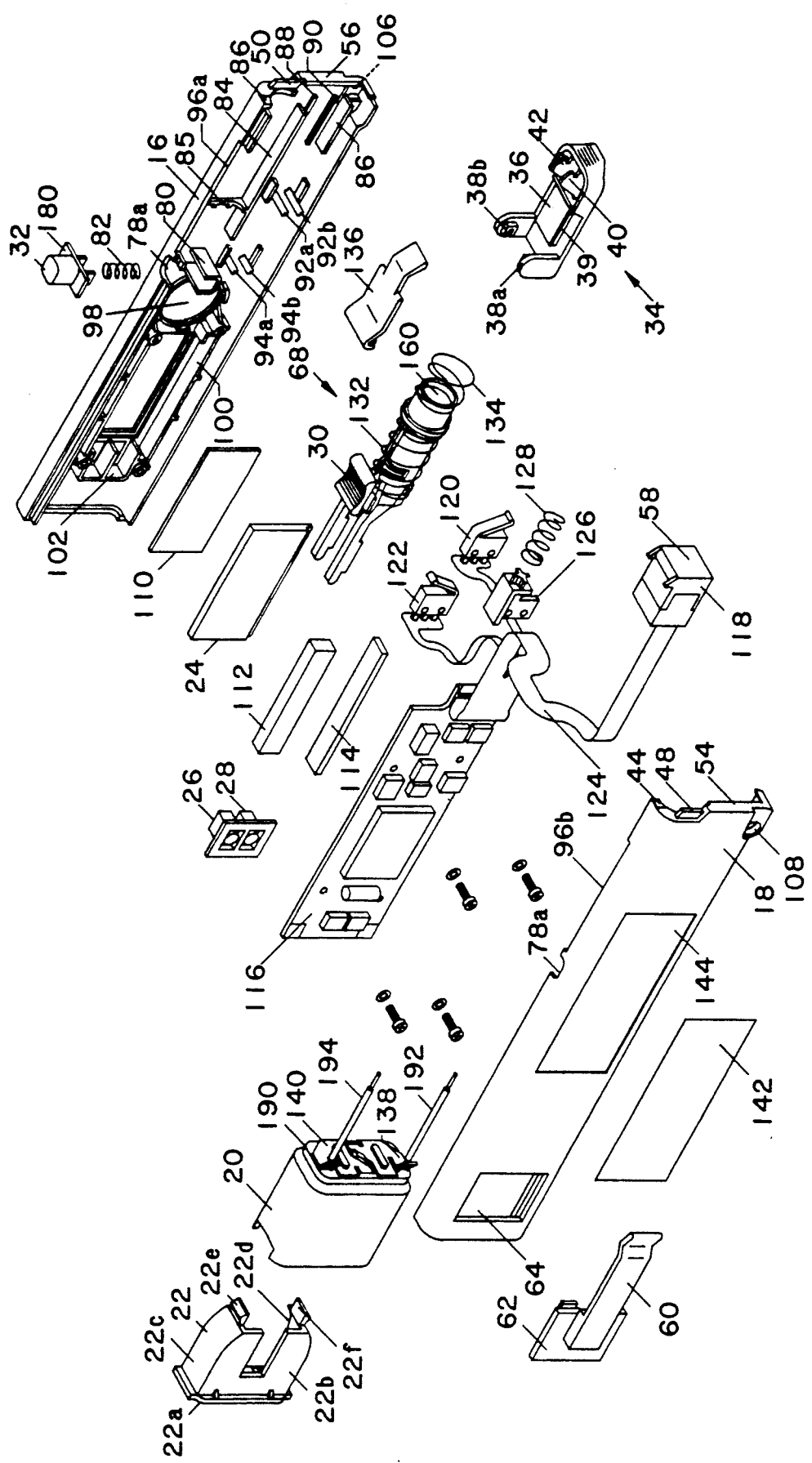
FIG. 5 illustrates an exploded view in perspective of the medical diagnostic system.

FIG. 5 illustrates an exploded view in perspective of the portable pocketable glucose medical diagnostic system 10, where all numerals correspond to those elements previously described. The front housing half 16 includes a release cutout 78a a spring containment channel 80, a release button spring 82 between the spring containment channel 80 and the release button 32, a supported horizontally aligned firing mechanism track member 84, a spring seat 85 between the firing mechanism track member 84 and the top of the housing member 16, an optics head track member 86, side spacer bars 88 and 90, switch mounts 92a-92b and switch mount 94a-94b. A slotted cutout 96a and release cutout 78a align along the top inner edge of the front housing half 16 and a slotted cutout 96b and a release cutout 78b align along the top inner edge of rear housing half 18 to accommodate movement of the release button 32 vertically and the actuator button 30 horizontally. The rear housing half 18 also includes mirror like image elements of the firing mechanism track member 84 and the spring seat 85 and the optics head track member 86. The front housing half 16 also includes a piezo sounding device mount 98, a rectangular bracket 100, a bracket 102 for mounting of a conductive rubber keypad 104 containing buttons 26 and 28 and pivot hole 106 at the lower end. The rear housing half 18 also includes a pivot hole 108. Pivot holes 106 and 108 in housing halves 16 and 18 accommodate the pivot blocks 38b and 38a of the dust cover 34 respectively. A clear plastic display window 110 and the LCD panel 24 align and secure in the rectangular bracket 100 a foam pad 112 and an elastomeric LCD connector 114 align between the LCD panel 24 and electronics circuit board 116. The electronics circuit board 116 connects to an optics head 118, a switch 120, and a switch 122 through a flex cable 124. An optics spring retainer 126 and an optics spring retainer 128 align behind the optics head 118 as later illustrated. The optics head 118 aligns between the firing mechanism track member 84 and the optics head track member 86 on the front housing half 16 and corresponding track members on the rear housing member 18. The firing mechanism assembly 68 aligns between the firing mechanism track member 84 and the top portion of the front and rear housing halves 16 and 18 and include the actuator button 30, a lancet carrier 130 a firing spring 132 and a return spring 134. A switch actuator 136 aligns between the optics head track member 86 and the bottom of the front housing half 16 and also between the corresponding members on the rear housing half 18. A positive and negative battery contact assembly 138 and 140 align and secure to the battery case 20. A user label 142 aligns in a label mount recess 144 on the rear housing half 18.

Figure 6:
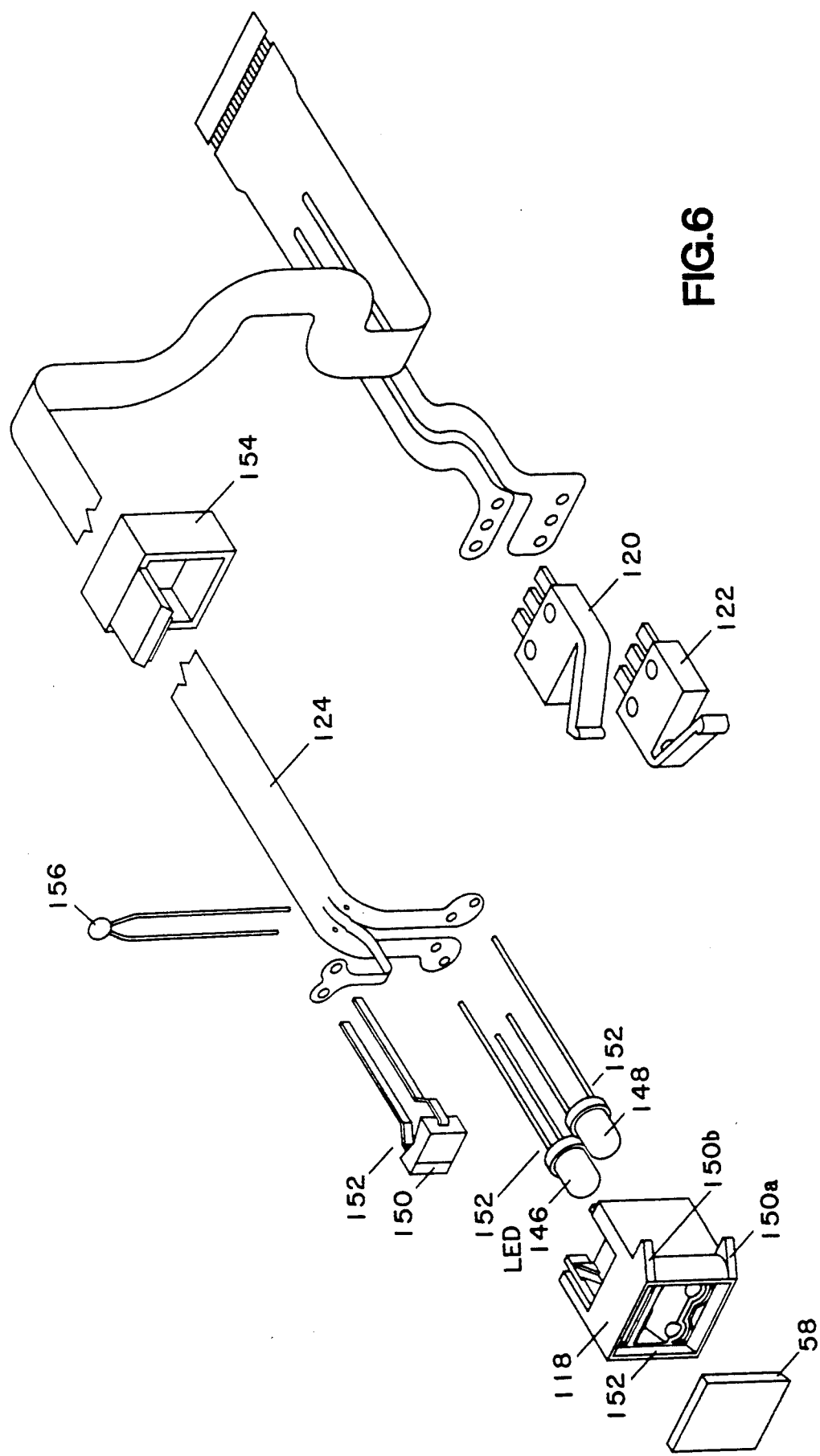
FIG. 6 illustrates an exploded view in perspective of the optics head.

FIG. 6 illustrates the optics head 118 and associated components where all numerals correspond to those elements previously described. The assembly is illustrated on its side for clarity of illustration. An LED 146, an infrared LED 148 and a photo diode 150 secure within the optics head 118 with adhesive units 152 and are canted at an angle. The optics head includes ramped surfaces 150a-150b extending from the surface 152 of the cube like optics head 118. These ramped surfaces 150a-150b assist in the sliding action of the optics head 118 when the disposable diagnostic reagent unit 12 is inserted into the portable pocketable glucose medical diagnostic system 10. An optics cover 154 fits over and about the optics head 118. A thermister 156 attaches to the flex cable 124.

Figure 7:
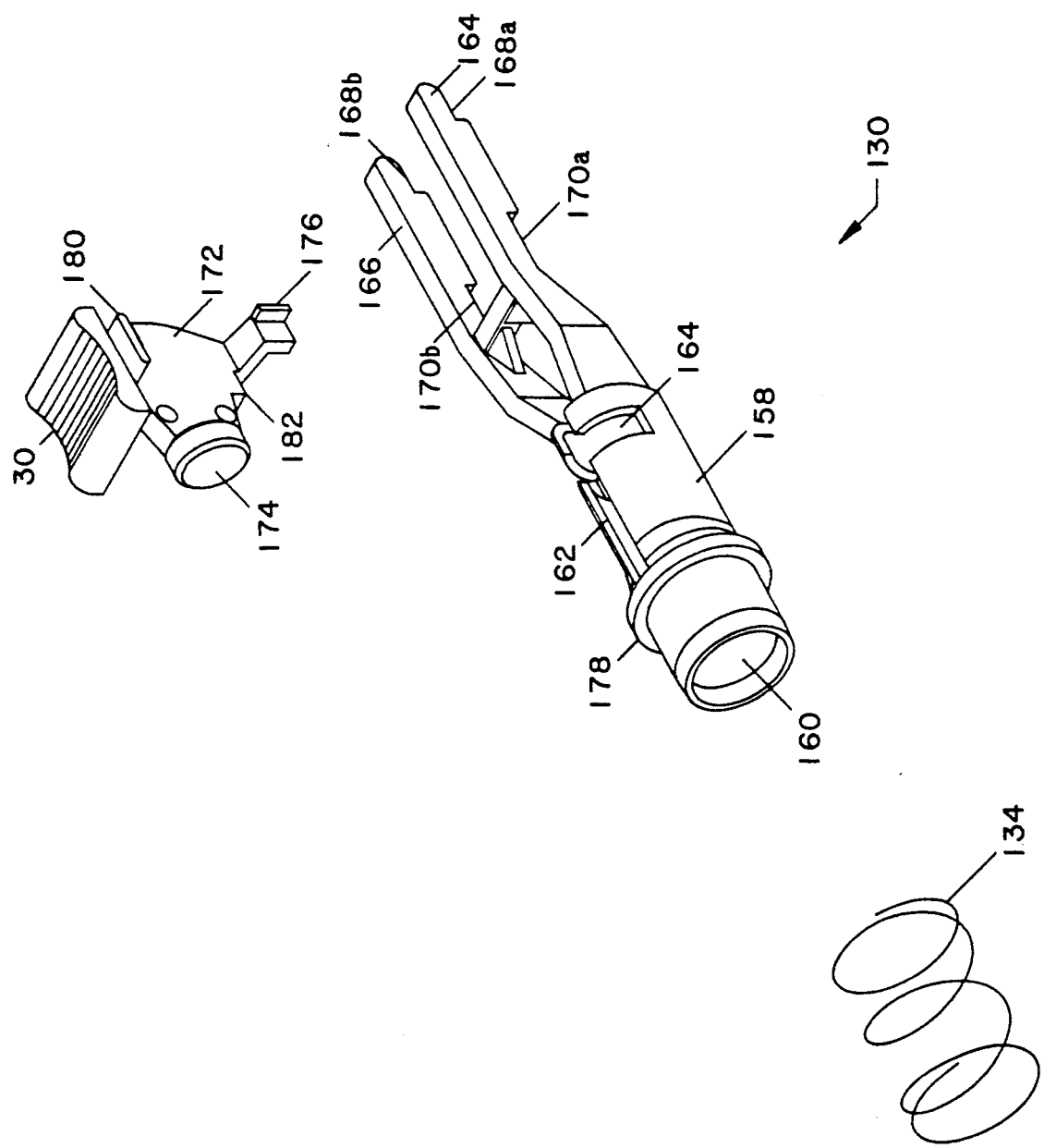
FIG. 7 illustrates an exploded view in perspective of the firing mechanism assembly.

FIG. 7 illustrates an exploded view of the firing mechanism assembly 68 where all numerals correspond to those elements previously described. The lancet carrier 130 is the nucleus of this assembly and includes a cylindrical body 158, an interior lancet cavity 160, a longitudinal horizontally aligned slot 162 in the upper portion of the cylindrical body 158, a vertically aligned slot 162 across the cylindrical body 158 and intersections the longitudinal horizontally aligned slot 162, detented actuator bars 164 and 166 including rear detents 168a and 168b and forward detents 170a and 170b. The actuator button rests atop a hammer body 172. A hammer 174 aligns on one edge of the hammer body 172. A cam 176 for actuation of the switch 122 extends laterally to the side of the hammer body 172. The hammer body 172 and hammer 174 fit in and slide within the lancet cavity 160. A spring seat 178 in the form of a ring is molded about the circumference of the cylindrical body 158. The firing spring 132 fits over and about the cylindrical body between the spring seat 178 and the hammer body 172 as illustrated in FIG. 8. The return spring 134 seats between the spring seat 178 and the end of the housings 16 and 18 as illustrated in FIG. 8. A planar member 180 aligns between the actuator button 30 and the hammer body 172. At the continuous slot between the planar member 180 and the actuator button 30 rides along slots 96a and 96b in the case halves 16 and 18 and serves to keep the hammer aligned in the lancet cavity 160.

FIG. 8 illustrates a perspective view of the dust cover where all numerals correspond to those elements previously described. Illustrated in particular is the color reference calibration strip 36 which aligns to the rectangular frame 39. Pivot blocks 38a and 38b are integral to and extend inwardly from the pivot bar members 184 and 186. Opposing pivot bar members 184 and 186 extend vertically from the main body 188 as to the latches 40 and 42. Pivot blocks 38a and 38b engage pivot holes 108 and 106 respectively of FIG. 5.

FIG. 9 illustrates a perspective view of the battery case 20, where all numerals correspond to those elements previously described. Positive and negative battery contact assemblies 138 and 140 include spring contactors 138a and 140a which frictionally engage a plastic securing plate 190 in the end of the battery case 20. The spring contactors 138a and 140a contact batteries 66a-66n which are held in the battery cover 22 of FIG. 3. Wies 192 and 194 are electrically connected to and extend from the battery contact assemblies 138 and 140 and connect to the electronics circuit board 116.

Figure 10:
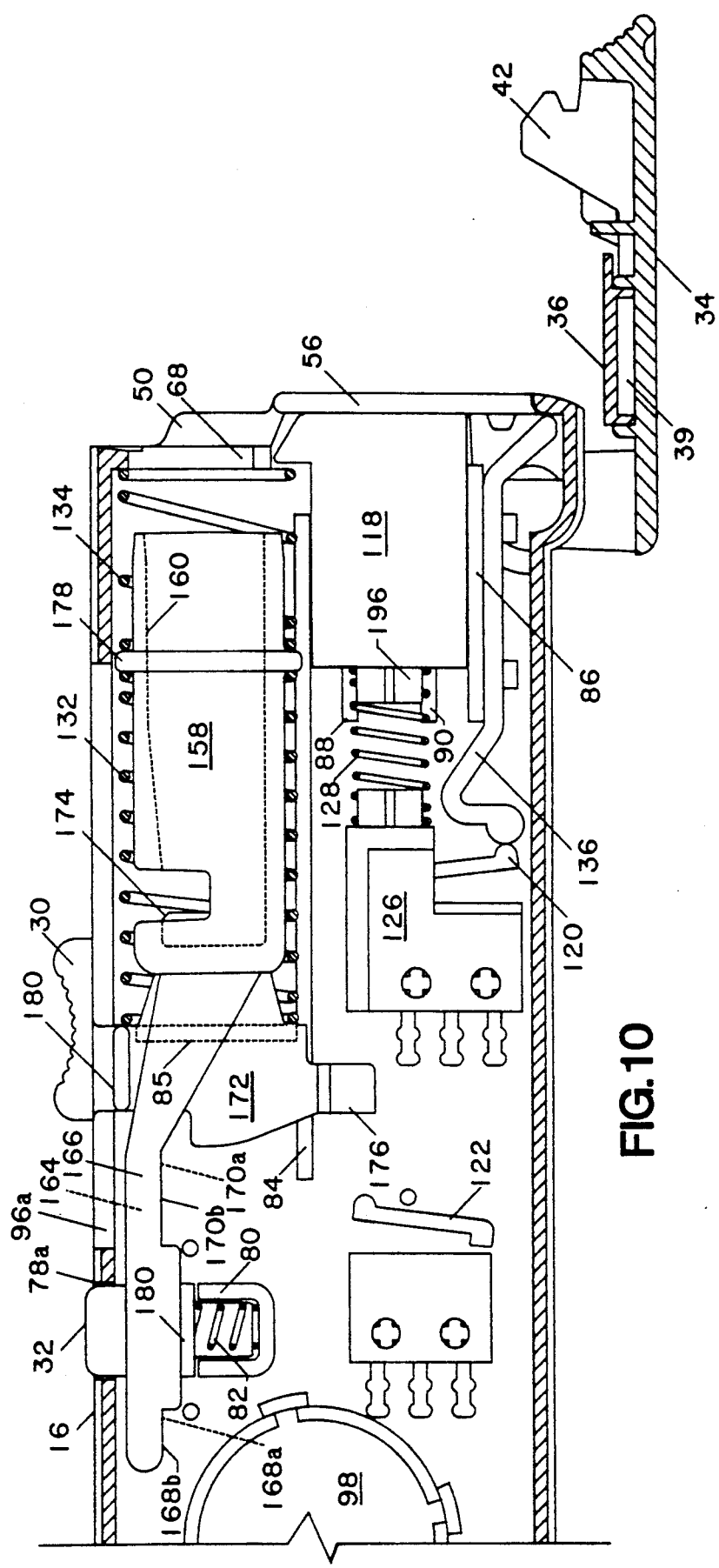
FIG. 10 illustrates a side view in partial cross section of the medical diagnostic system.

FIG. 10 illustrates a side view in partial cross section of the medical diagnostic system 10, where all numerals correspond to those elements previously described. The cylindrical body 158 with the included and internally aligned hammer body 172 align between the top of the case, the firing mechanism track member 84, and the front position of the front and rear housing halves 16 and 18. Firing springs 132 and return spring 134 both seat against opposing sides of the spring seat 178 on the cylindrical body 158. The return spring also seats around and about the material surrounding the orifice 68. The firing spring seats against the spring seat 85 of the hammer body 172, slides within the lancet cavity 160, in the cylindrical body 158, and contacts engages and compresses the firing spring 132, when moved to the right in this illustration. The hammer body 172, including the cam 176 are actuated along longitudinal axis by the sliding of the actuator button 30. As the cylindrical body 158 is positioned longitudinally the attached detented actuator bars 164 and 166, are longitudinally positioned to engage or disengage detents 168a–168b and 170a–170b, upon both sides of the planar member 180, on the release button 32. A spring 82, seats in the spring containment channel 80 and against the interior of the release button 32 to spring the release button 32 outwardly. The release button 32 aligns in the release cutouts 78a and 78b also illustrated in FIG. 5. The actuator button 30, including the planar member 180 captures the edges of the case halves 16 and 18 adjacent to slotted cutouts 98a and 96b illustrated in FIG. 5. The cam 176 actuate the optics head switch 122 at it rear most travel. The optics head 118 aligns along the side spacer bars 88 and 90 and the optics head track member 86 of the front housing half 16 and corresponding members on the rear housing half 18. A spring alignment post 196 is included on the rear side of the optics head and another spring alignment post 198 is included on the optics spring retainer 126. A spring 128, aligns over the spring alignment posts 196 and 198 to slideably retain the optics head 118, in a position to the right of the spring and against the vertical end bars 56 and 54 found also in FIG. 5. A switch actuator bar 136 is actuated against the optics head switch 120 as later described in detail.

Figure 11:
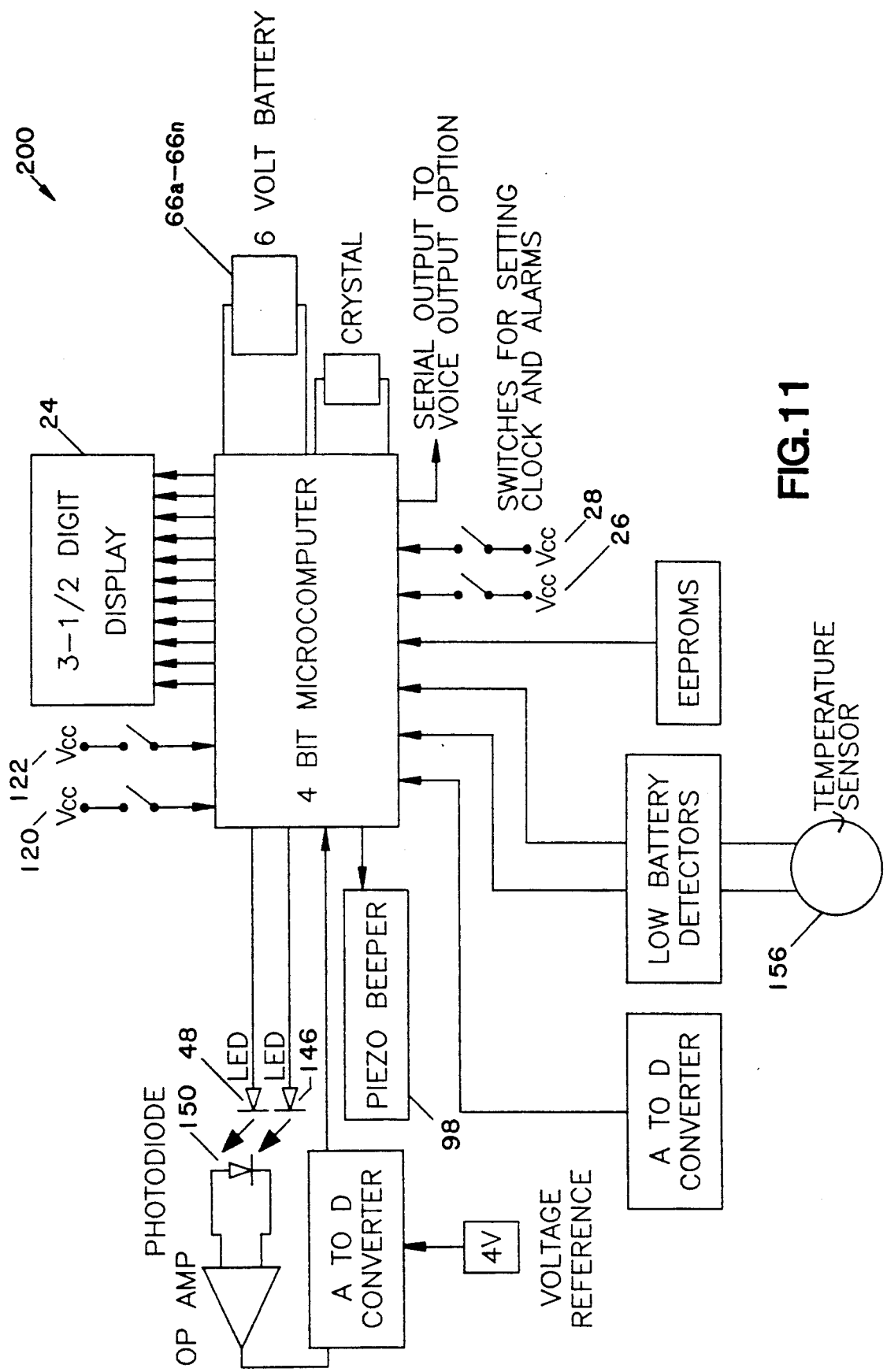
FIG. 11 illustrates a block diagram of the medical diagnostic system.
Figures 1, 12A:
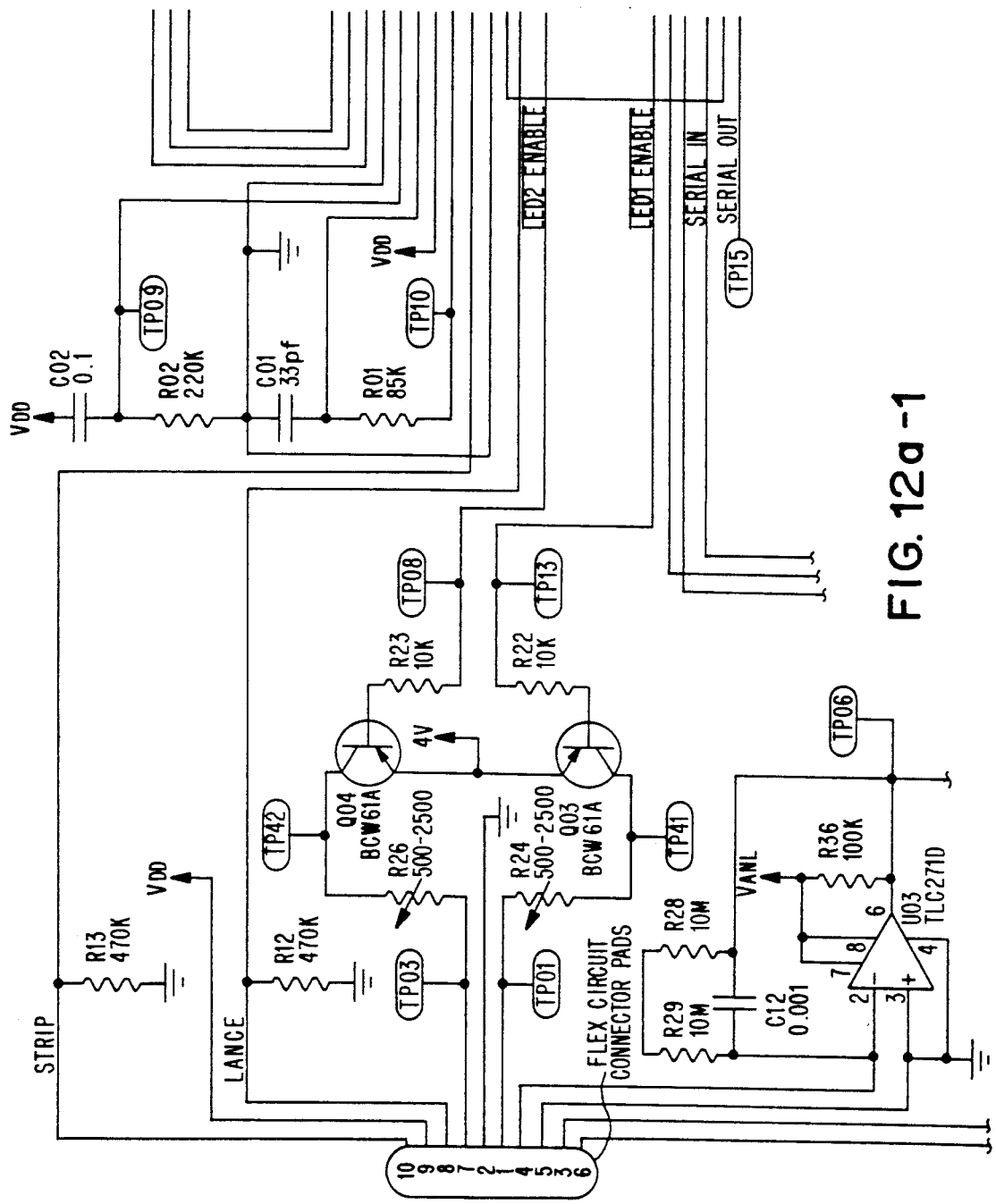
Figures 2, 12A:
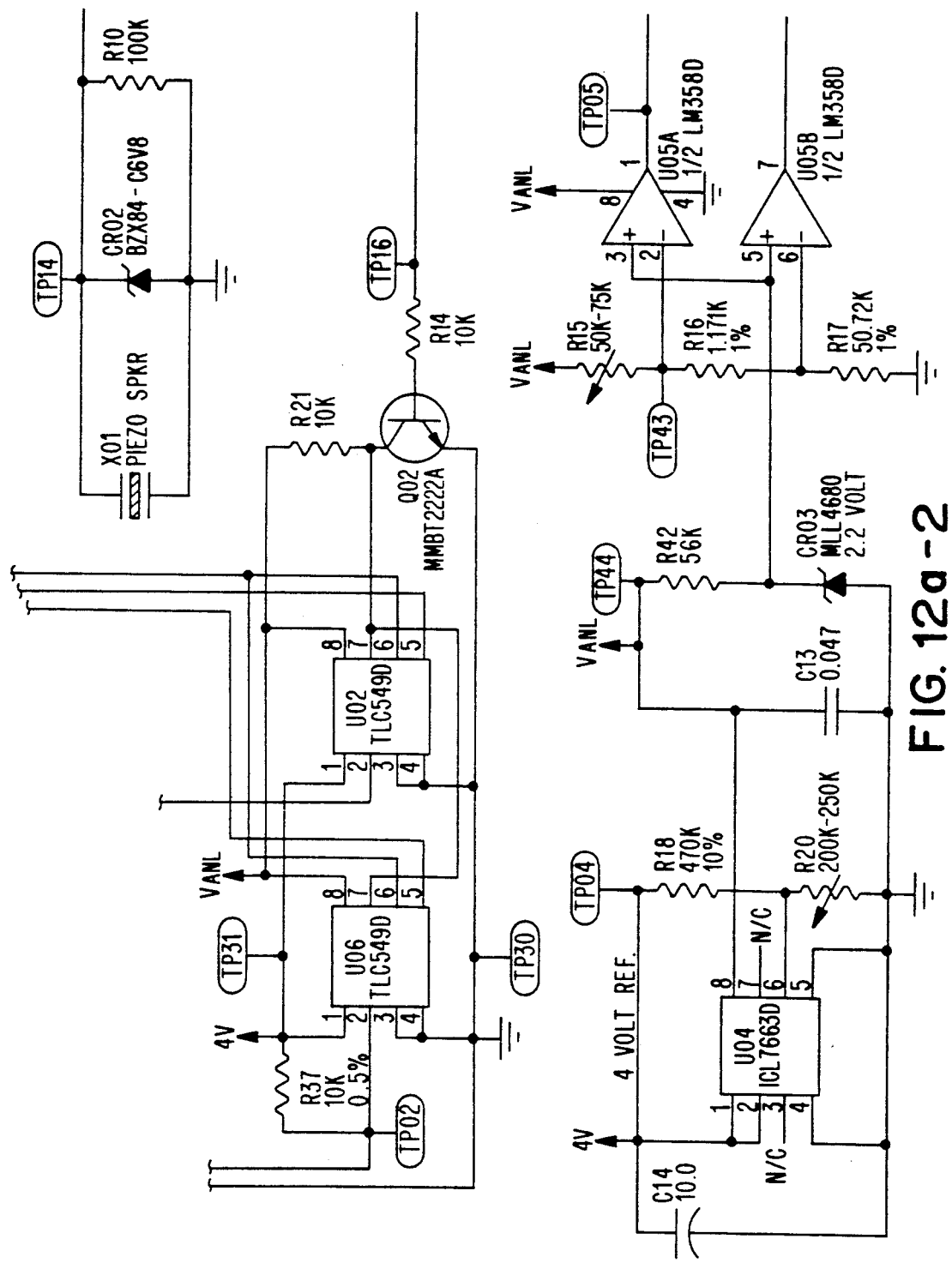
Figures 1, 12B:
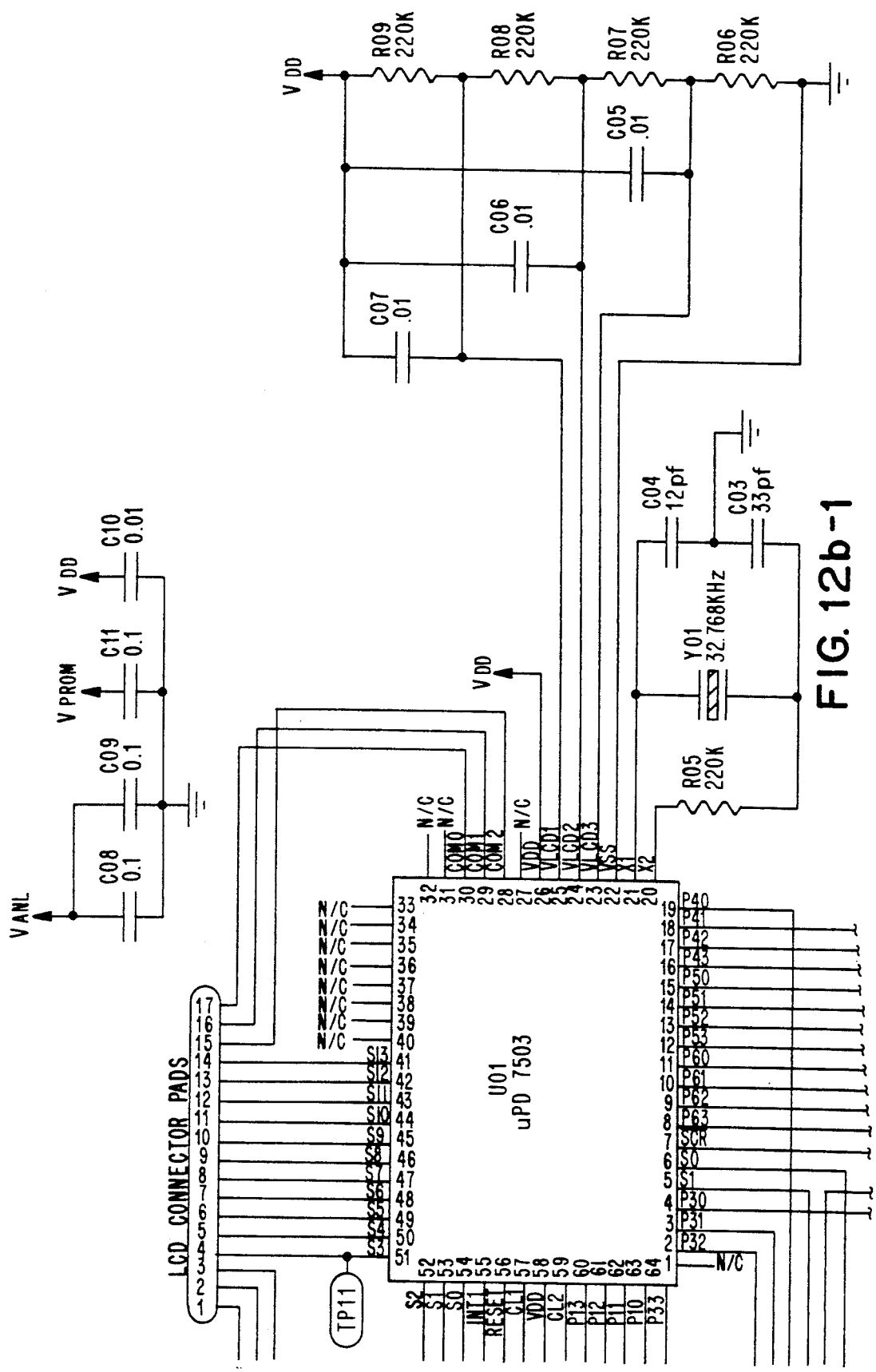
Figures 2, 12B:
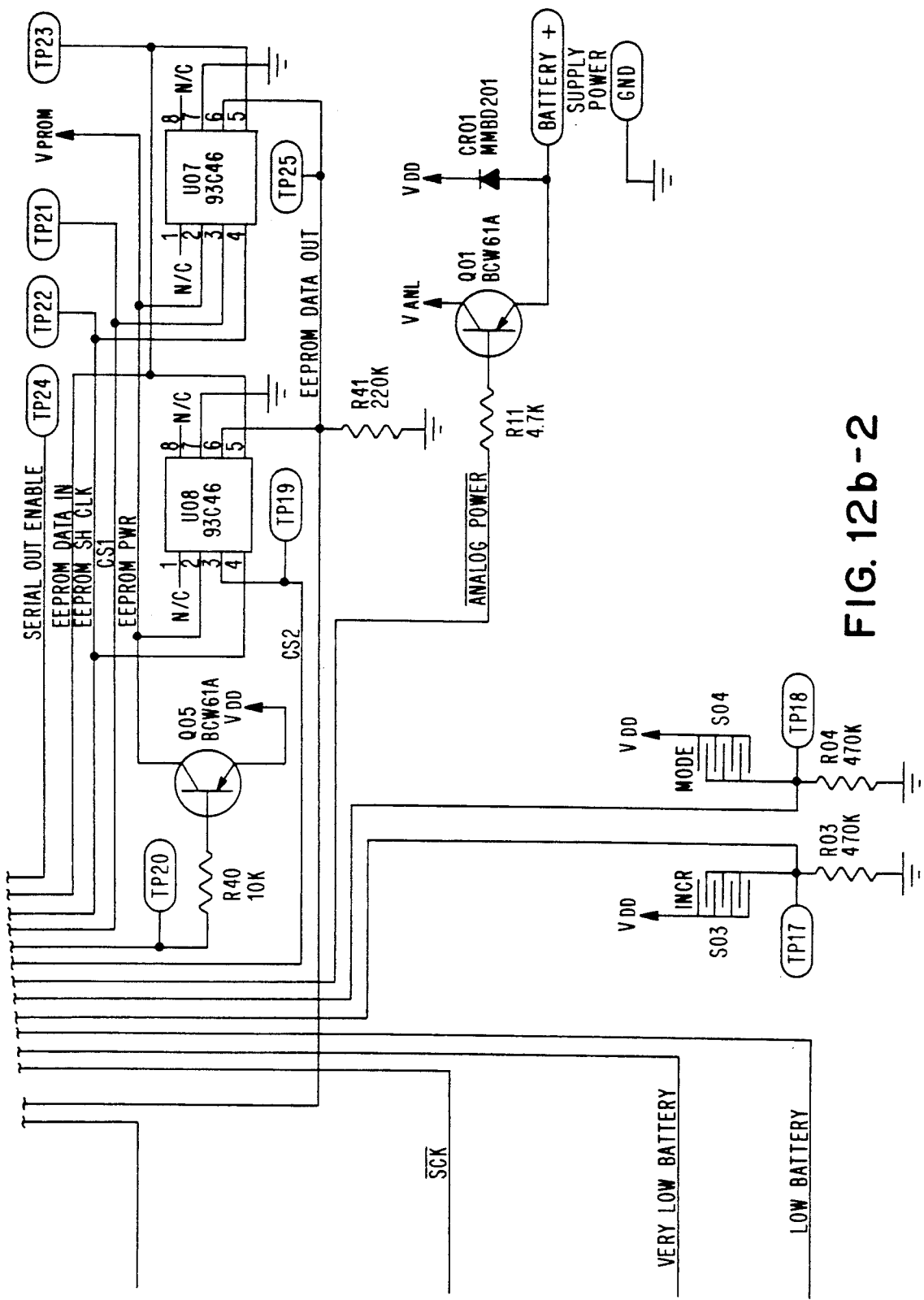
Figure 12C:
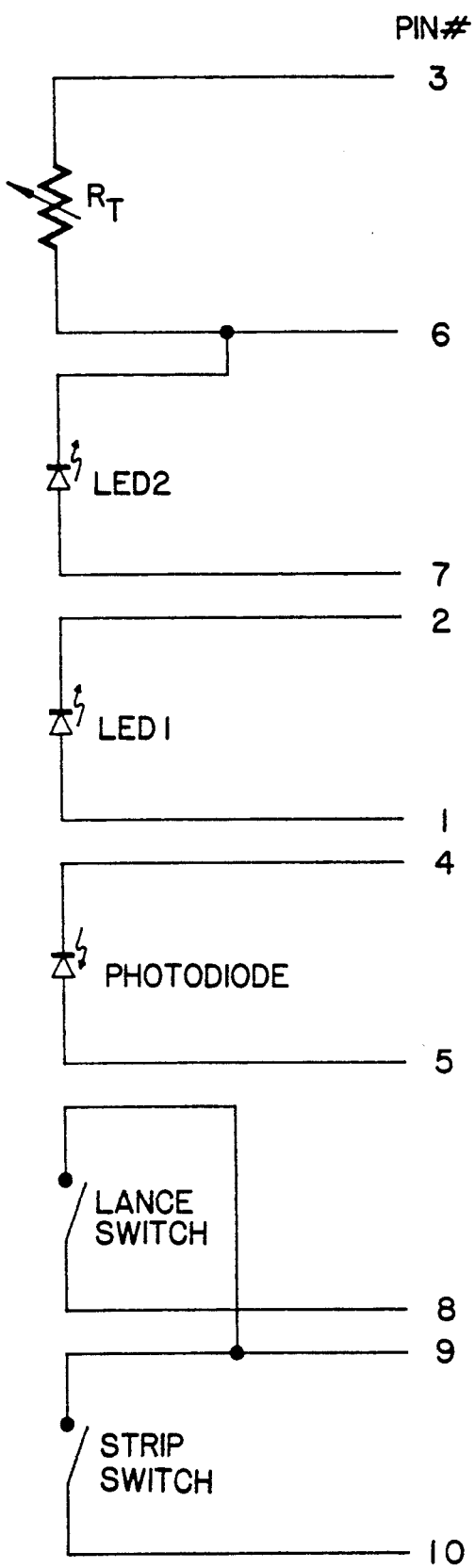

FIG. 11 illustrates and electrical block diagram of the medical diagnostic system, where all numeral correspond to those elements previously described and as now described in FIGS. 12a, 12b and 12c.

FIGS. 12A1–12A2, 12B1–12B2 and 12C illustrate the electrical circuit schematic package diagram 201, including the digital display 202, clock and alarm switches 203 and 204, light emitting diodes 205 and 206, photo diode 207, strip switch 208, lance switch 209, piezo electric beeper 210, and batteries 211 and 212. A high gain opamplifier 213 including, op-amp feedback capacitor 214, and op-amp pull-up resistor 215 are for the amplifier circuit. A to D converter 216, inverter transistor 217 for clock for A to D converter 216, pull-up resistor 218 for inverter 217, inverter transistor base drive resistor 219, voltage reference regulator integrated circuit 220, voltage reference regulator input bypass capacitor 224, output adjustment resistor 222, output adjustment potentiometer 223, output filter capacitor 221, voltage reference resistor 225, and voltage reference diode 226 are for the A to D conversion of the several colorimetric change of the reagent and the voltage reference regulator. Switching transistor 237 for LED 205, switching transistor 238 for LED 206, switching transistor base drive resistor 273, and switching transistor base drive resistor 274, are for switching the LED's, LED 205 brightness adjustment resistor 240, LED 206 brightness adjustment resistor 239, are for compensating the LED's. RC oscillator circuit capacitor 245, RC oscillator circuit resistor 246, reset capacitor 243 and reset resistor 244 are for the microprocessor 249. Piezo electric beeper impedance load resistor 232, microprocessor pull-down resistor 241, microprocessor pull-down resistor 242, microprocessor pull-down resistor 247, microprocessor pull-down resistor 248, analog power switching transistor 271, switching transistor base drive resistor 270, reverse voltage protector diode 272, 32.768 KHZ crystal for timer 255, timer current limiter resistor 254, crystal oscillator capacitor 256, and crystal oscillator capacitor 257 are for the microprocessor 249. A to D converter 233 for temperature variations, thermistor 273, and voltage divider resistor 234 are for the temperature sensing circuit. LCD bias resistors 261–264 and LCD bias capacitors 258–260, are for LCD display 202. Serial data output enable jack 275, serial data output jack 281, and serial data clock jack 282 are for external connections such as to a personal computer. Bypass capacitors 205–253, low battery and very low battery comparators 230, and comparator voltage dividers 227–229 are for power supply circuitry. EEPROM power transistor 266, and EEPROM power base resistor 265, control power to serial EEPROM 267 and 268.

The operation of the electrical circuitry of FIGS. 12a and 12b is now described in detail. LED 205 is the light source that illuminates the reagent chemistry area. The reagent chemistry changes color in proportion to the amount of glucose in the blood. The light from LED 205 reflects off the chemistry and is sensed by photodiode 207. This signal is amplified by a high gain op-amp 213, and then sent to the input of the analog to digital converter 216. The analog signal is converted to a digital signal for use by microprocessor 249. The software algorithms in microprocessor 249 processes this information, and then outputs a blood glucose measurement to the liquid crystal display 202.

LED 206 is the light source that illuminates the lot to lot indicator on the medical diagnostic system 10. This provides information to the microprocessor 249 to correct for variations in different lots of chemistry. The lot to lot indicator also is used to determine if blood has completely covered the reagent chemistry. The reflected light from LED 206 is sensed by photodiode 207, and the signal is sent to the microprocessor 249 in the same way as light reflected from LED 205.

Voltage reference regulator 220, provides a reference voltage for the medical monitoring system circuitry. The reference voltage is used by the analog to digital converter 216, the low battery detection comparators 230, temperature A to D converter 233 and also to keep the LED outputs constant.

Comparators 230 are used to provide a low battery and very low battery signal to the microprocessor 249. Switching transistor 271 is used to control the power to the analog circuitry which is turned on only when the photodiode 207 sensing circuits are active. A crystal 255 provides a precision clock to the microprocessor 249 for the various timing functions. Switch 209 is used to initiate a blood glucose measurement sequence by the medical monitoring system 10. Switch 208 provides the microprocessor 249 with a signal to tell when a reagent unit 12 is inserted. Switches 203 and 204 are used to set the clock and four alarms on the medical monitoring system 10. The piezo electric beeper 231 provides an audible beep to indicate test progress or error conditions. Thermistor 273 with A to D converter 233 provide temperature correction input data to microprocessor 249 to correct for ambient temperature variations which may occur in the user's environment. EEPROMs 267 and 268, provide non-volatile memory storage for alarms, saved glucose reading and various coefficients used in microprocessor 249, calculations.

FIG. 13 illustrates the loading of the medical diagnostic system 10, mode of operation with a reagent unit 12, where all numerals correspond to those elements previously described.

FIGS. 14a–14i illustrate the component positioning and mode of electromechanical operation for the medical diagnostic system 10, where all numerals correspond to those elements previously described.

Figure 14A:
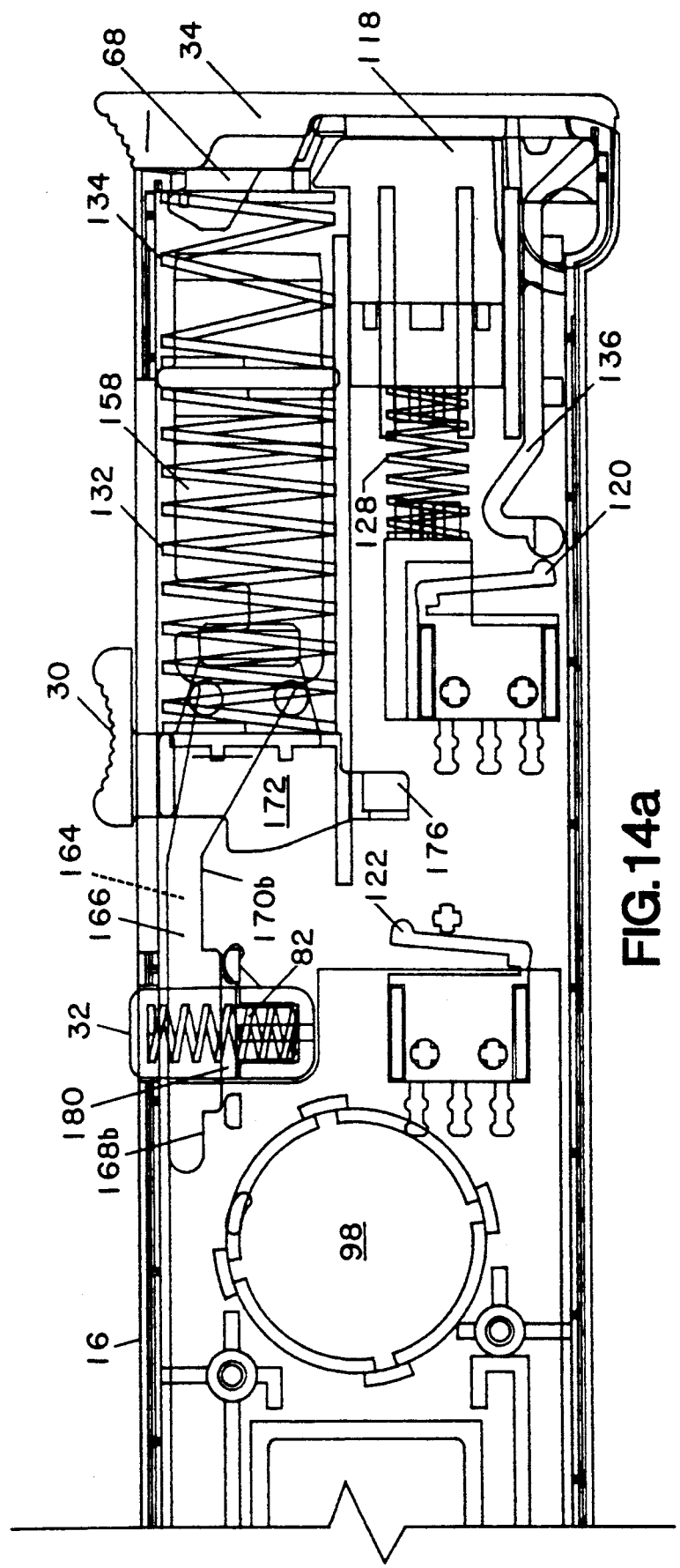
Figure 14B:
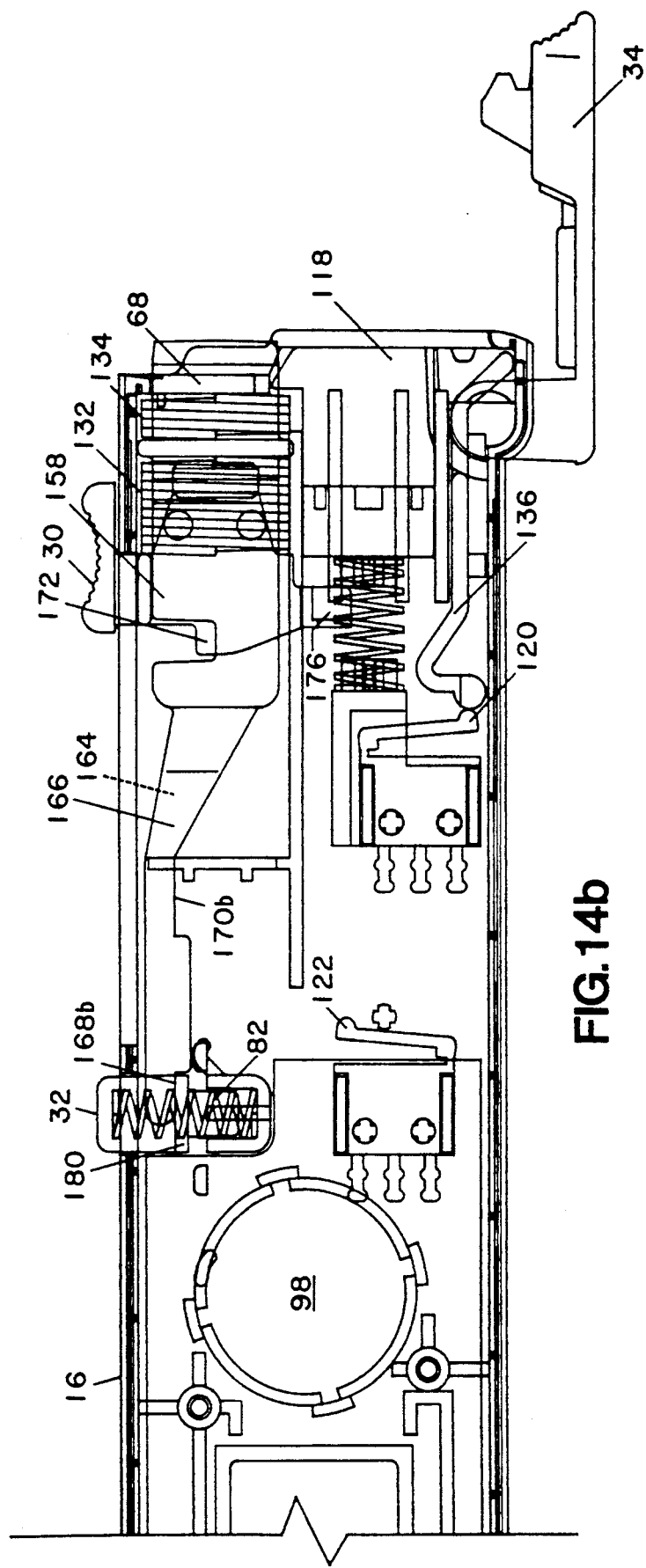
Figure 14C:
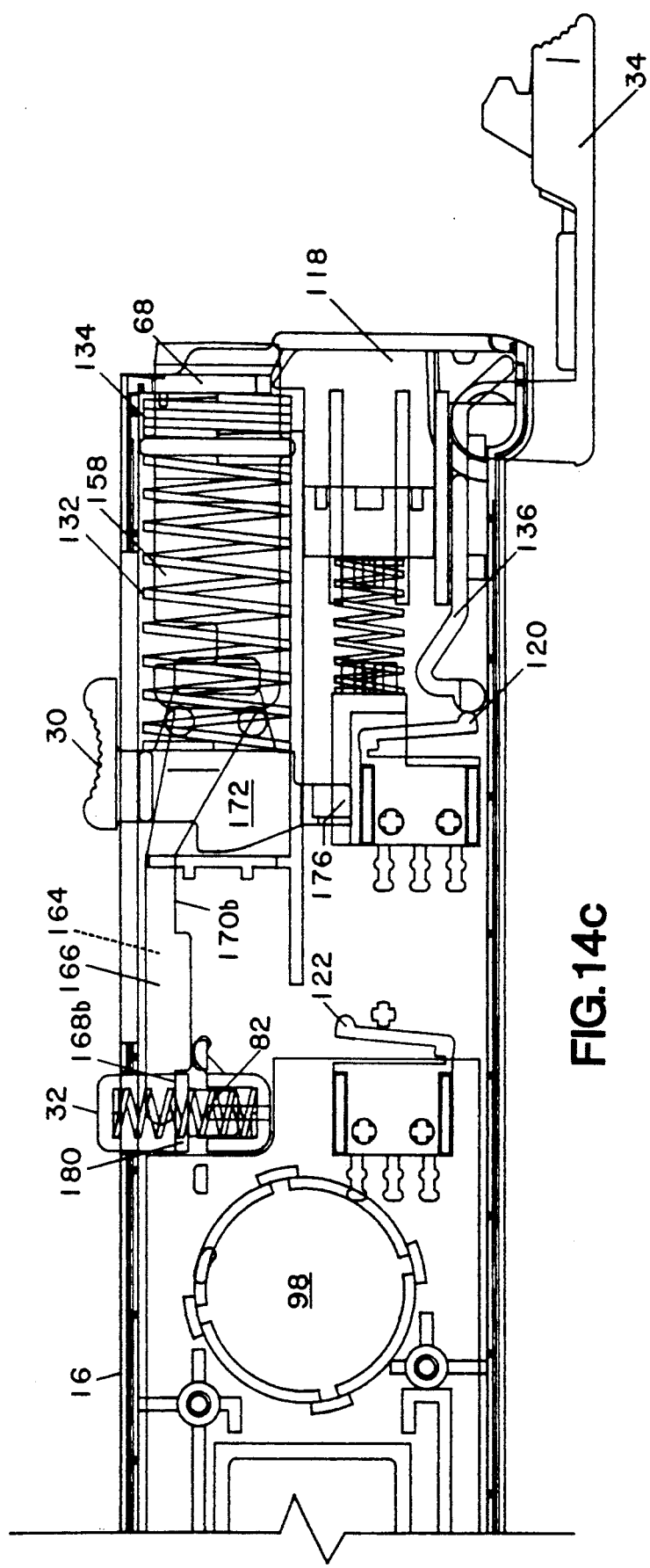
Figure 14D:
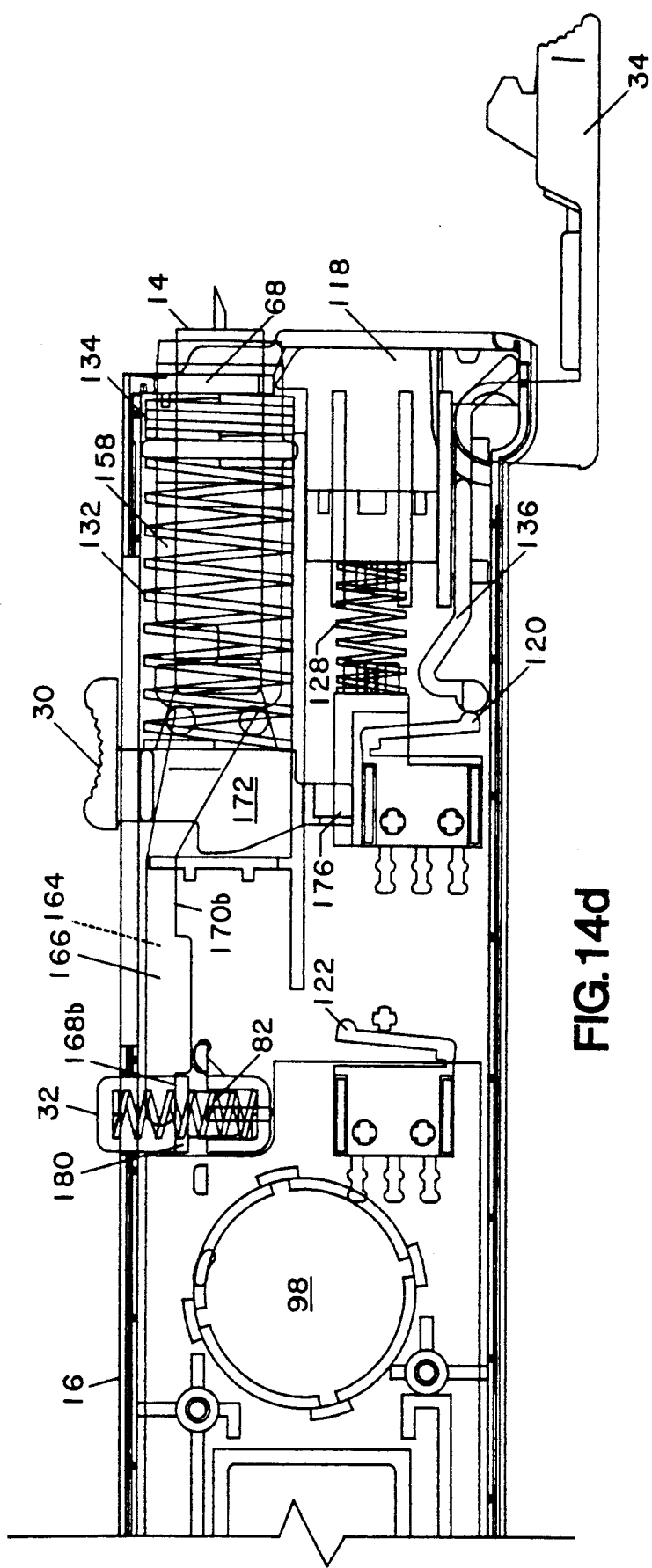
Figure 14E:
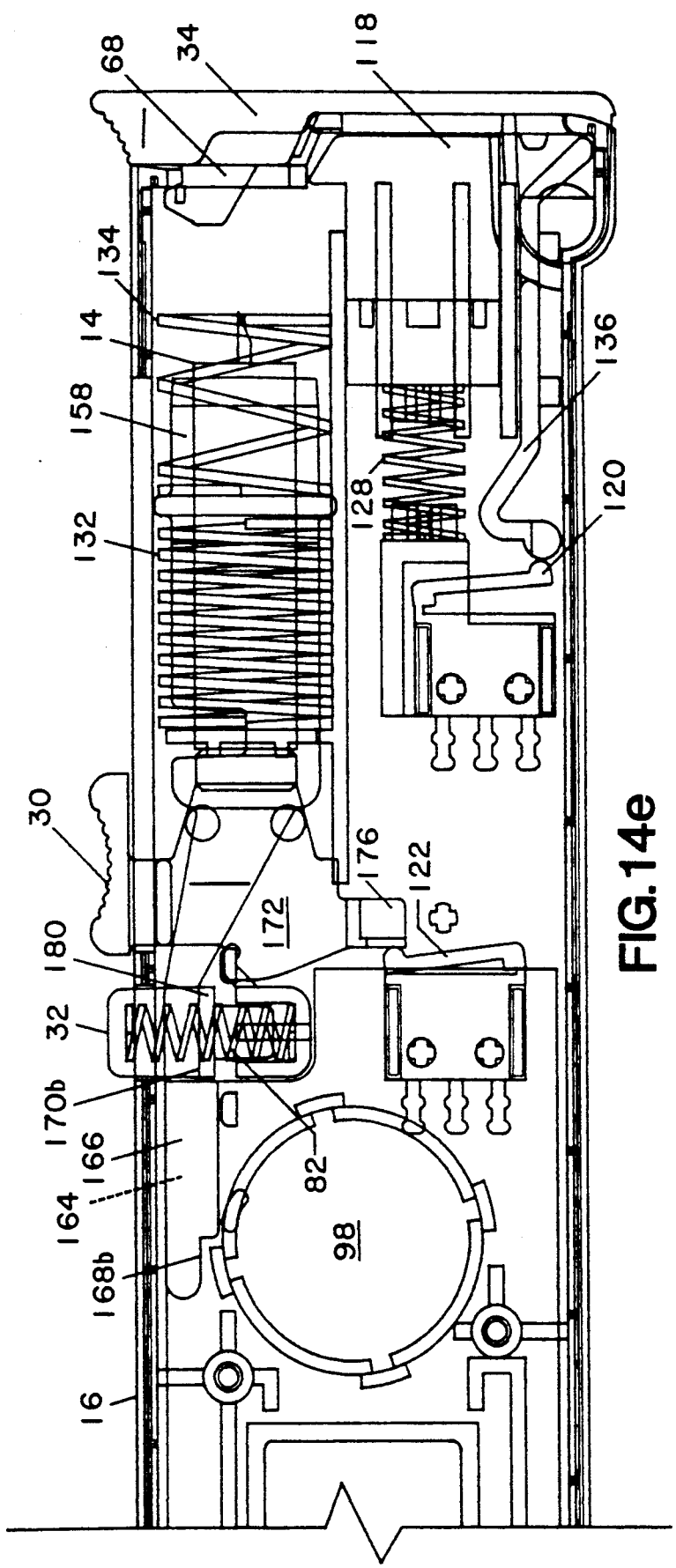
Figure 14F:
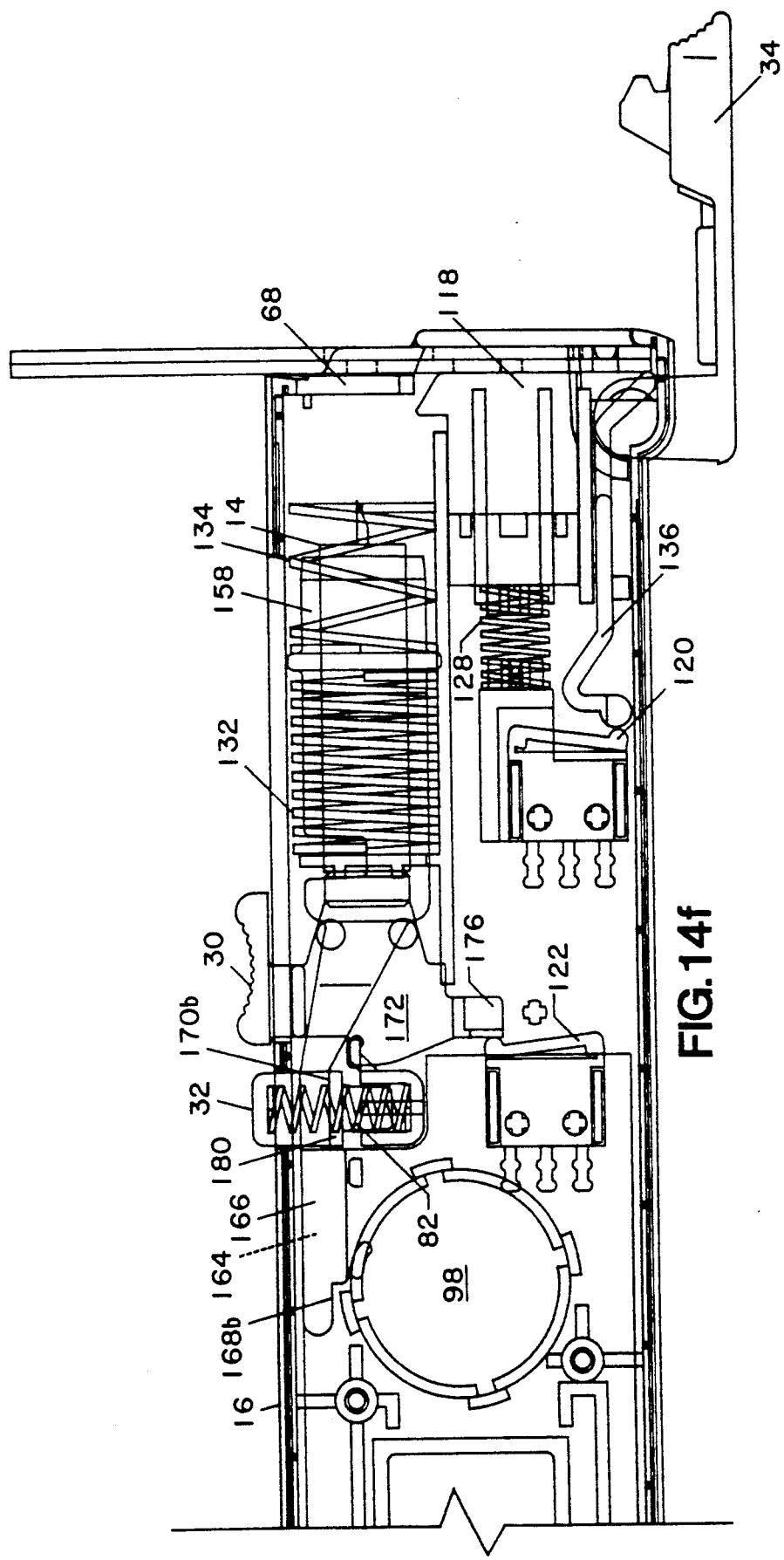
Figure 14G:
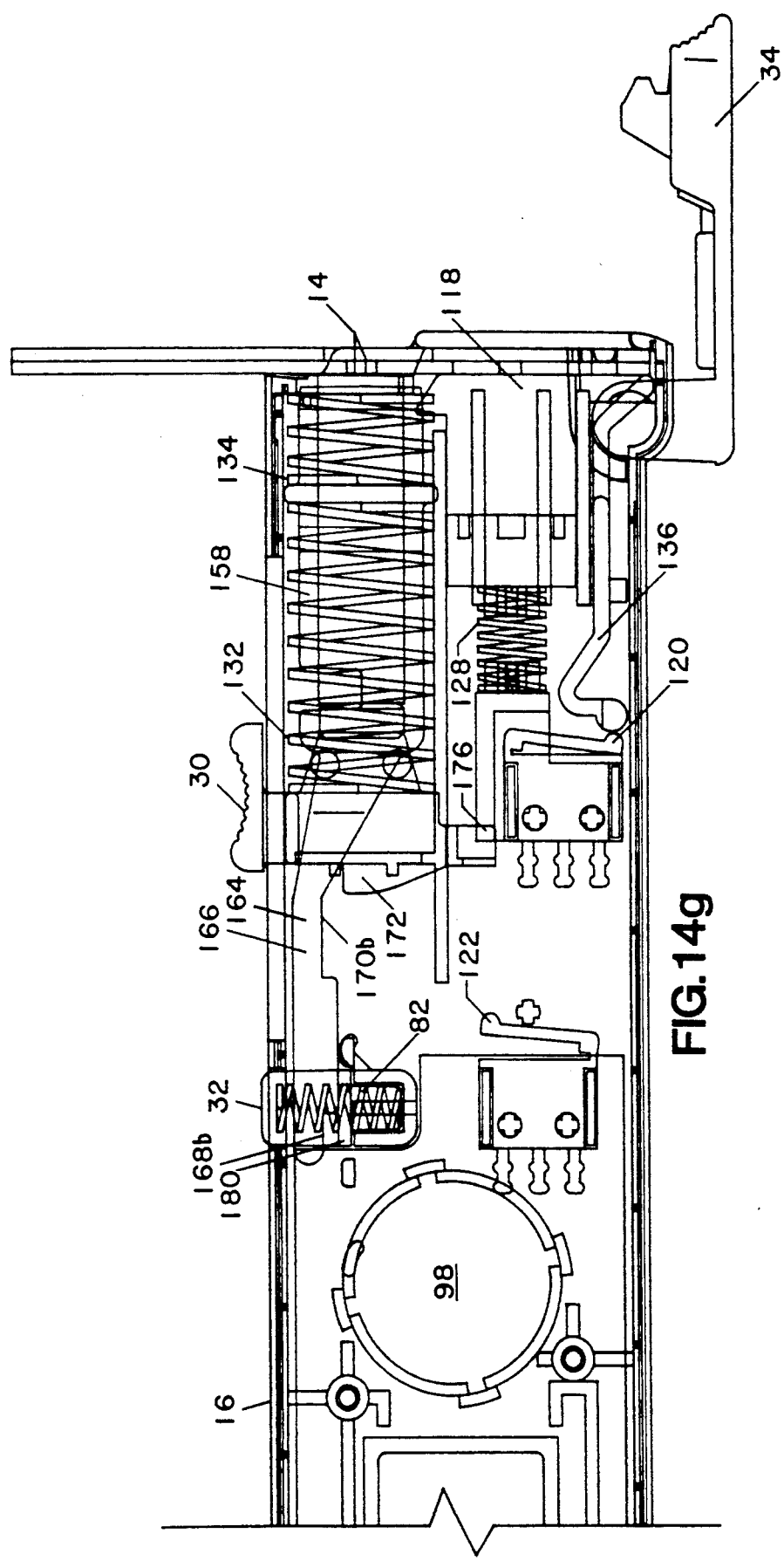
Figure 14H:
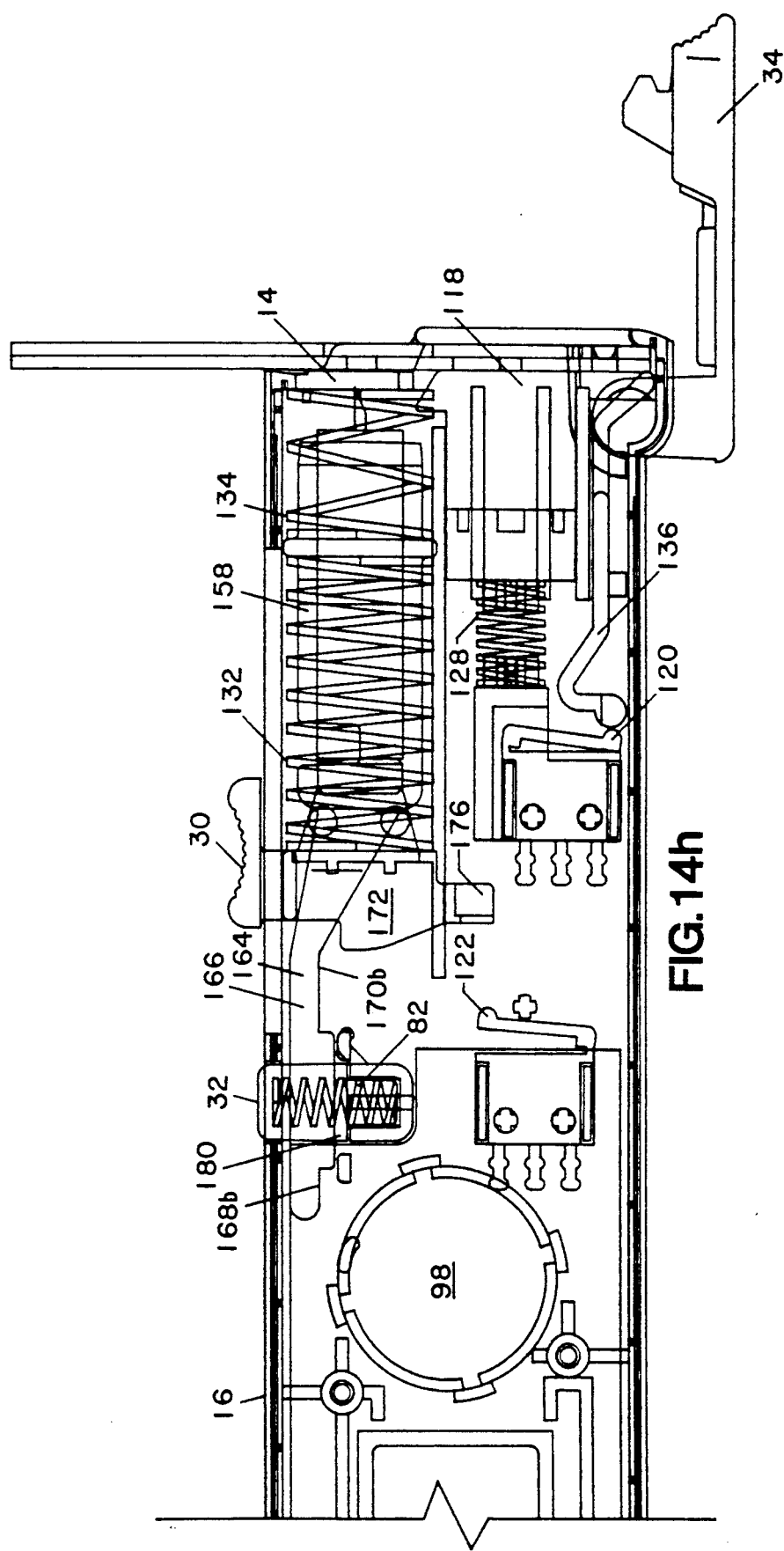
Figure 14I:
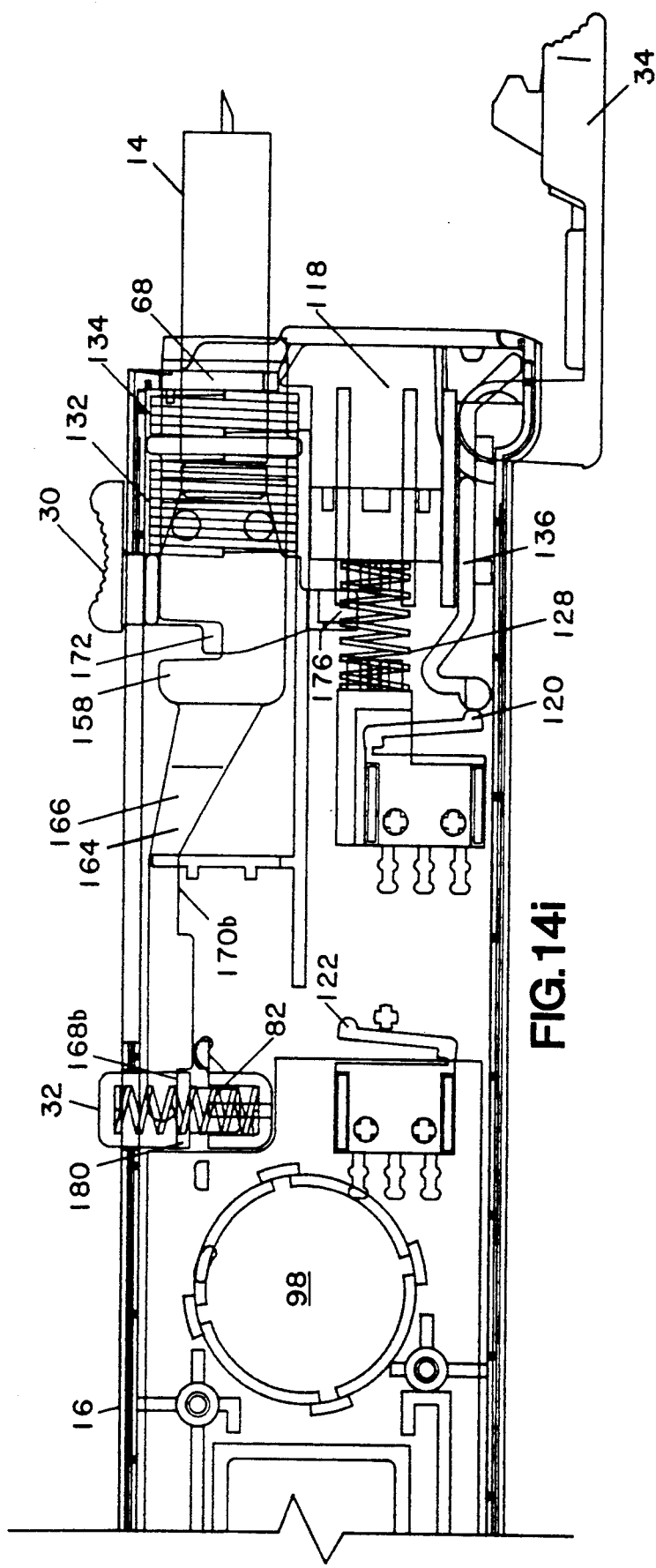
Figure 16A:
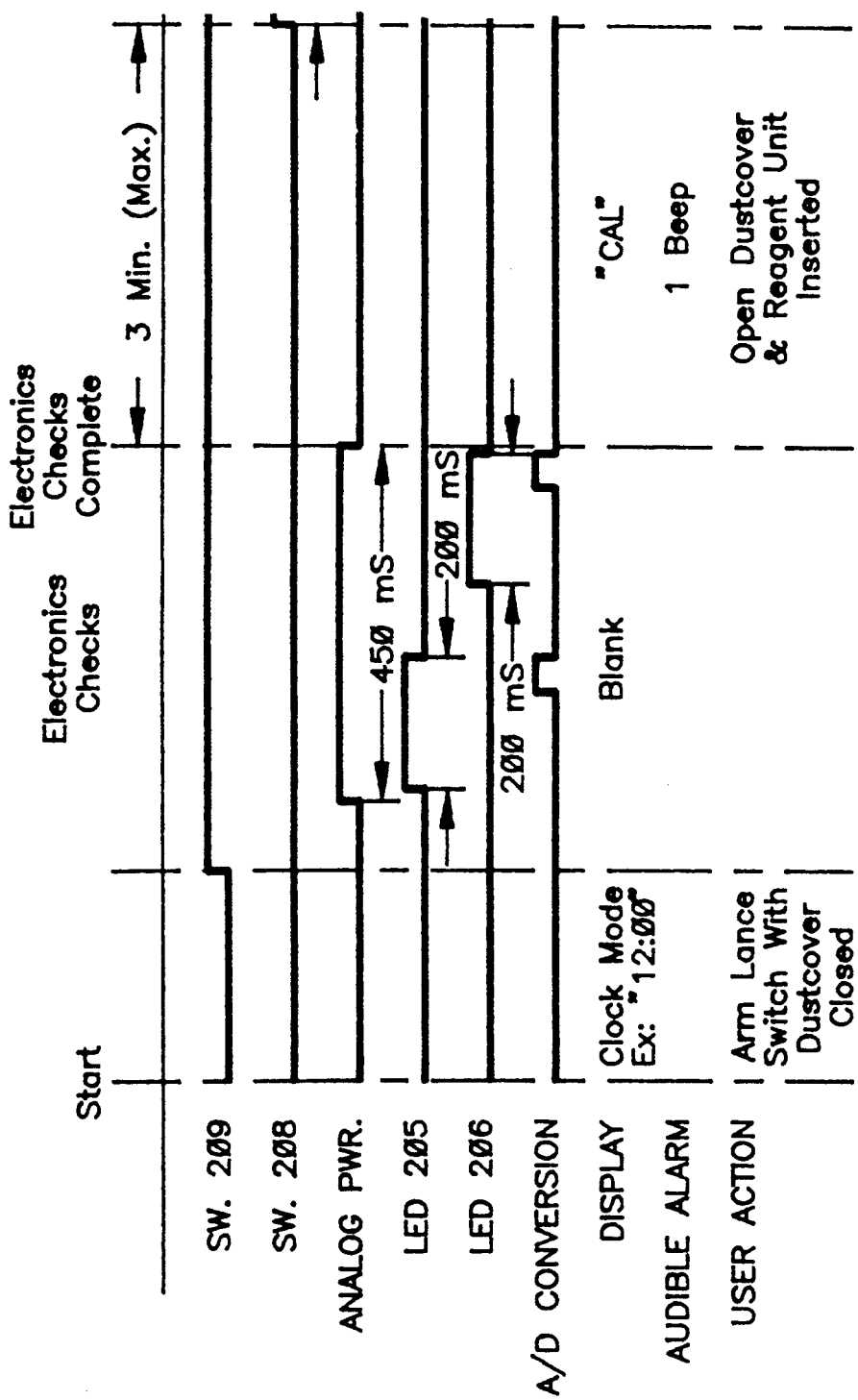
Figure 16B:
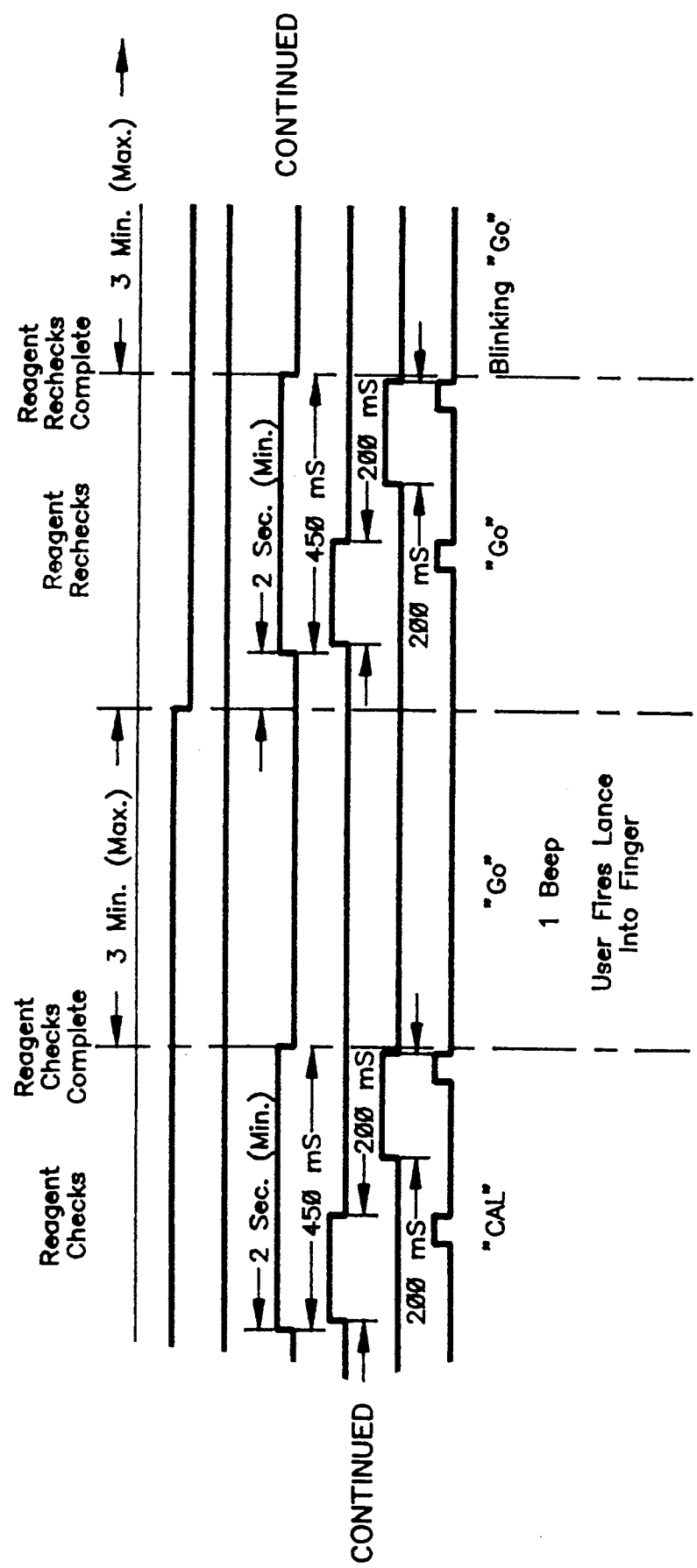
Figure 16C:
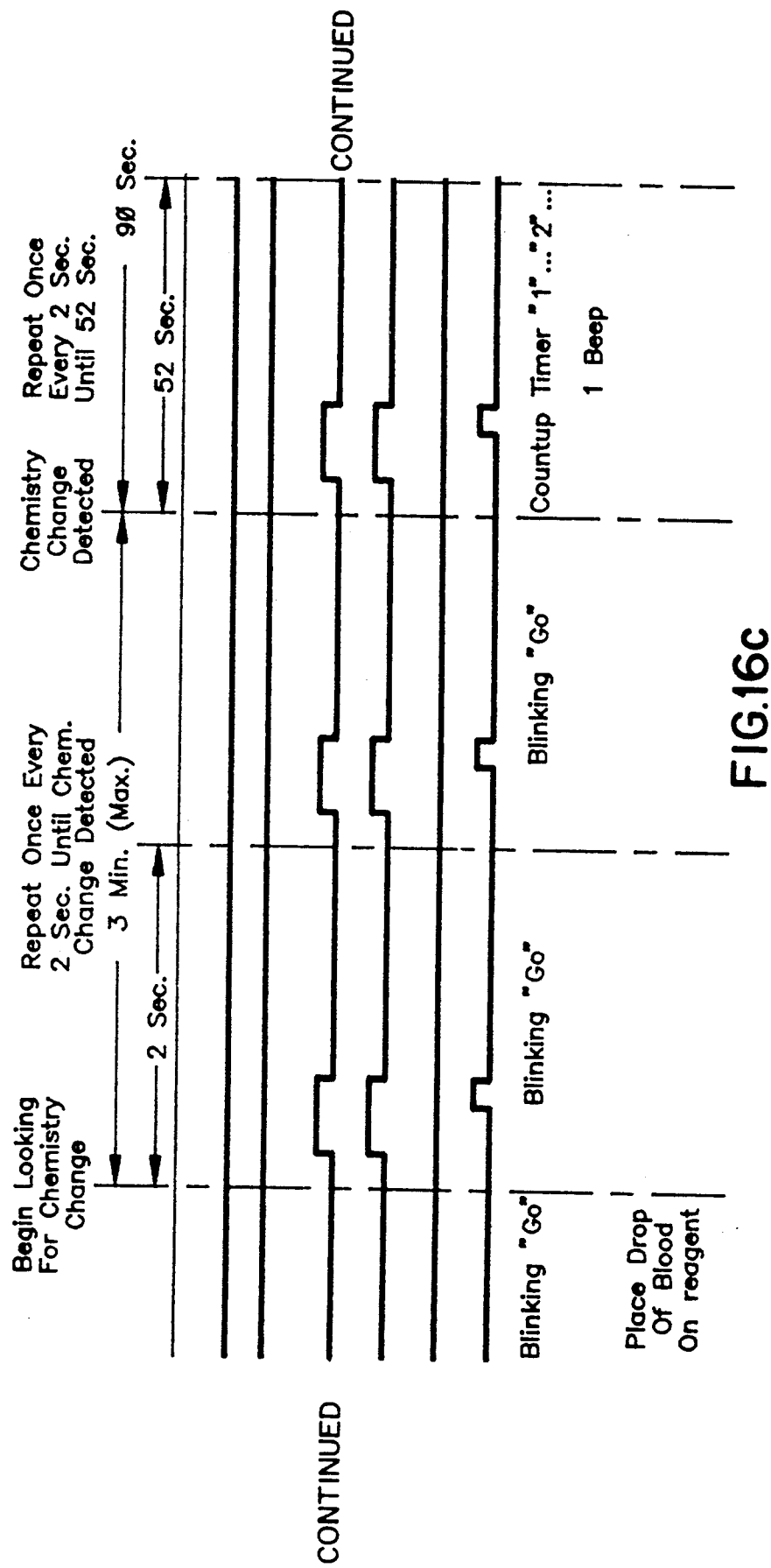
Figure 16D:
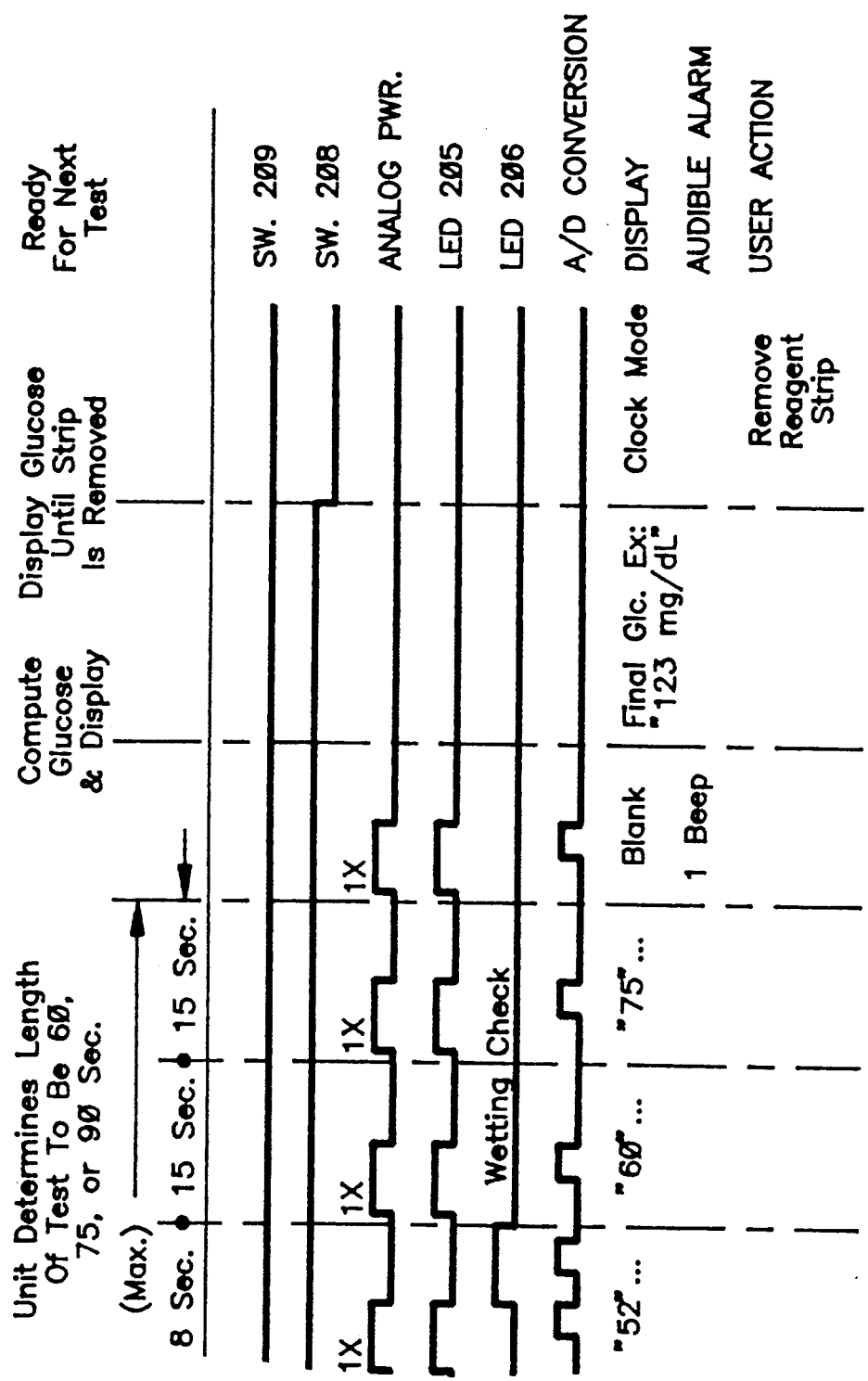

FIG. 14a illustrates normal position of the elements;

FIG. 14b illustrates the actuator button pushed into loading position;

FIG. 14c illustrates the button released and locked in a loading position;

FIG. 14d illustrates a lancet inserted while in a loading position;

FIG. 14e illustrates a button pressed into a cocked position;

FIG. 14f illustrates a strip inserted:

FIG. 14g illustrates a full extended position during penetration;

FIG. 14h illustrates a returned to normal position after penetration; and,

FIG. 14i illustrates the button pressed into an ejection position for removing and ejecting the lancet.

In operation, push the sliding button forward. Insert the lancet into the carrier tube. Remove the cap, press the release button. With the optic cover closed, pull back the sliding button. Open the optic cover and insert the reagent unit into position. Press a finger firmly on the reagent unit collector. Press the release button and squeeze the finger for hanging a drop of blood. Place on wick in the blood bowl. Read the glucose value displayed after 90 seconds, and record the results. Pull out and discard the used reagent unit. Push the sliding button forward to eject the used lancet, and close the optic cover.

FIG. 15 illustrates display messages generated by algorithms in the microprocessor for display in the LCD.

FIGS. 16A-D illustrates a timing diagram of the electrical components in conjunction with the electromechanical components.

The operation of the medical diagnostic system with the reagent unit, is also described in a manual filed with the patent specification.

Various modifications can be made to the present invention without departing from the apparent scope hereof. The system can be programmed to detect these types of changes besides color changes, as is through the teaching of this disclosure.

We claim:

1. System for extraction and analysis of a component of a liquid, said system receiving a disposable diagnostic reagent unit which exhibits a color change on sensing a predetermined component in the liquid, said system comprising:

a. optical measurement means including a light source and light sensor for measuring light emanating from said source and reflected by reagent chemistry in said unit and having an optical characteristic proportional to the component of a liquid to be measured after transporting said liquid to said reagent;

b. said optical measurement means also for generating an electrical signal responsive to a change of said reagent chemistry and therefore also to the component to be measured;

c. microprocessor means for processing said generated electrical signal;

d. display means responsive to said processed signal for providing a visual readout representative of the analysis on said display means in said housing member; and, e. means for removably receiving a disposable diagnostic reagent unit including said reagent chemistry.

2. System for extraction and analysis of a component of blood in a body, said system receiving a disposable diagnostic reagent unit which exhibits a color change on sensing a predetermined condition, said system comprising:

a. housing member including a spring actuated hammer means in said housing member for driving a lancet and a disposable lancet removably positioned on said hammer means;

b. optical measurement means including a light source and light sensor for measuring light emanating from said source and reflected by blood reagent chemistry in said unit and having an optical characteristic proportional to the component of a liquid to be measured after transporting said liquid to said reagent;

c. said optical measurement means also for generating an electrical signal responsive to a change of said blood reagent chemistry and therefore also to the component to be measured;

d. microprocessor means for processing said generated electrical signal;

e. display means responsive to said processed signal for providing a visual readout representative of the analysis on said display means in said housing member; and, f. means for removably receiving a disposable diagnostic reagent unit including said blood reagent chemistry.

3. Hand-held pocketable medical monitoring diagnostic system for extraction and analysis of a component of blood in a body, said system comprising:

a. pocketable housing member including a spring actuated hammer means in said housing member for driving a means for puncturing and a disposable lancet removably positioned on said hammer means;

b. optical measurement means including a light source and light sensor for measuring light emanating from said source and reflected by blood reagent chemistry having a color optical characteristic proportional to the component of a liquid to be measured when in contact with said liquid;

c. said optical measurement means for generating an electrical signal responsive to a color change of said blood reagent chemistry and therefore also to the component to be measured;

d. microprocessor means for processing said generated electrical signal;

e. display means responsive to said electrical signal for providing a visual readout representative of the analysis on said display means in said housing member;

f. means for removably receiving a disposable diagnostic reagent unit; and, g. disposable diagnostic reagent unit for operative engagement in said receiving means of said glucose medical monitoring diagnostic system, said unit including housing means for operatively connecting said unit to said receiving means of said system, said blood reagent chemistry supported within said housing, at least one opening in said housing means includes means for said means for puncturing to pass through and means for transporting a liquid substance to said blood reagent chemistry, means for transporting said liquid substance to said blood reagent chemistry, and aperture means through said housing for reading a portion of said blood reagent chemistry whereby said blood reagent chemistry yields a responsive optical characteristic which is read by said optical measurement means, processed by said microprocessor means, and displayed by said display means thereby yielding a numerical value useful for diagnosing a condition.

4. The system of claim 3 wherein said transporting means is a wicking material.

5. The system of claim 3 wherein said blood reagent chemistry is glucose oxidase.

6. The system of claim 3 including means to return said hammer means to an original rest position.

7. The system of claim 3 including cocking means for storing energy in said spring and connected to said hammer means.

8. The system of claim 3 including means for excluding ambient light including a light-tight enclosure of said housing of said unit.

9. The system of claim 3 including a calibration sensor for sensing visual calibration color said reagent chemistry at predetermined times as sequenced by said microprocessor means.

10. The system of claim 3 including piezoelectric audio means, said audio means being connected to said microprocessor means for beeping on predetermined conditions.

11. The system of claim 3 wherein said microprocessor means includes means for displaying operational messages on said display means.

12. The system of claim 3 wherein said microprocessor means includes means for displaying a plurality of previous readings.

13. The system of claim 3 including a dust cover adjacent to said optical measurement means, and said dust cover including a calibration chart means for reading by said optical measurement means.

14. The system of claim 3 wherein said housing is rectangular.

15. The system of claim 3 including means for clipping into a shirt pocket of a user.

16. The system of claim 3 including means in said housing for allowing batteries to be replaced battery replacement.

17. The system of claim 3 including switch means on said housing and connected to said microprocessor means for setting and displaying time.

18. The system of claim 3 including means in said microprocessor for displaying numerical values in the English system and metric system.

19. The system of claim 3 wherein said microprocessor means includes a four bit microprocessor.

20. The system of claim 3 wherein said reagent chemistry is a solid.

21. The system of claim 3 wherein said optic measurement means comprises two LED's and a photodiode.

22. The system of claim 3 wherein said housing is of a size to comfortably fit in a users hand.

23. The system of claim 3 including a dust cover means rotatable on said housing for protecting said said optical measurement means.

24. The system of claim 23 including calibration means internally mounted on said dust cover means for reading by said optical measurement means.

25. The system of claim 24 including means in said microprocessor to verify LOT/LOT reagent specific calibration codes of said calibration means.

* * * * *